(12) United States Patent
Davis et al.

(10) Patent No.: US 11,865,030 B2
(45) Date of Patent: Jan. 9, 2024

(54) VARIABLE FIT FLUID COLLECTION DEVICES, SYSTEMS, AND METHODS

(71) Applicant: PureWick Corporation, El Cajon, CA (US)

(72) Inventors: Kathleen Davis, Atlanta, GA (US); Katie Grupp, Alpharetta, GA (US); Joanna Starkie, Cambridge (GB); Merissa Lim Sarrias, Hauxton (GB); Emily Lucy Triggs, Cambridge (GB); Samuel Edmund Whittome, Cambridge (GB)

(73) Assignee: PureWick Corporation, Covington, GA (US)

( * ) Notice: Subject to any disclaimer, the term of this patent is extended or adjusted under 35 U.S.C. 154(b) by 0 days.

(21) Appl. No.: 17/663,046

(22) Filed: May 12, 2022

(65) Prior Publication Data

US 2022/0339023 A1    Oct. 27, 2022

Related U.S. Application Data

(63) Continuation of application No. PCT/US2022/012794, filed on Jan. 18, 2022.

(60) Provisional application No. 63/138,878, filed on Jan. 19, 2021.

(51) Int. Cl.
*A61F 5/451* (2006.01)
*A61F 5/44* (2006.01)
*A61F 5/443* (2006.01)

(52) U.S. Cl.
CPC ............ *A61F 5/451* (2013.01); *A61F 5/4401* (2013.01); *A61F 5/443* (2013.01); *A61F 5/4408* (2013.01)

(58) Field of Classification Search
CPC ....... A61F 5/4401; A61F 5/4408; A61F 5/443
See application file for complete search history.

(56) References Cited

U.S. PATENT DOCUMENTS

| | | | |
|---|---|---|---|
| 670,602 | A | 3/1901 | Baker |
| 1,032,841 | A | 7/1912 | Koenig |
| 1,178,644 | A | 4/1916 | Johnson |
| 1,742,080 | A | 12/1929 | Jones |
| 1,979,899 | A | 11/1934 | O'Brien et al. |
| 2,262,772 | A | 11/1941 | Peder |
| 2,326,881 | A | 8/1943 | Packer |
| 2,379,346 | A | 6/1945 | Farrell |
| 2,613,670 | A | 10/1952 | Edward |
| 2,616,426 | A | 11/1952 | Adele |

(Continued)

FOREIGN PATENT DOCUMENTS

| | | |
|---|---|---|
| AU | 2018216821 A1 | 8/2019 |
| CA | 2165286 C | 9/1999 |

(Continued)

OTHER PUBLICATIONS

US 9,908,683 B2, 03/2018, Sandhausen et al. (withdrawn)

(Continued)

*Primary Examiner* — Guy K Townsend
(74) *Attorney, Agent, or Firm* — DORSEY & WHITNEY LLP

(57) ABSTRACT

Examples relate to fluid collection devices, systems, and methods of collecting fluid from wearers. The fluid collection devices include a retention means for maintaining the position of the fluid collection device with respect to the wearer.

26 Claims, 10 Drawing Sheets

(56) References Cited

U.S. PATENT DOCUMENTS

| | | | |
|---|---|---|---|
| 2,644,234 A | 7/1953 | Earl | |
| 2,859,786 A | 11/1958 | Tupper | |
| 2,968,046 A * | 1/1961 | Duke | A61G 9/006 604/149 |
| 2,971,512 A | 2/1961 | Reinhardt | |
| 3,032,038 A | 5/1962 | Swinn | |
| 3,077,883 A | 2/1963 | Hill | |
| 3,087,938 A | 4/1963 | Hans et al. | |
| 3,194,238 A | 7/1965 | Breece | |
| 3,198,994 A | 8/1965 | Hildebrandt et al. | |
| 3,221,742 A | 12/1965 | Egon | |
| 3,312,981 A | 4/1967 | McGuire et al. | |
| 3,349,768 A | 10/1967 | Keane | |
| 3,362,590 A | 1/1968 | Gene | |
| 3,366,116 A | 1/1968 | Huck | |
| 3,398,848 A | 8/1968 | Donovan | |
| 3,400,717 A | 9/1968 | Bruce et al. | |
| 3,406,688 A | 10/1968 | Bruce | |
| 3,424,163 A | 1/1969 | Gravdahl | |
| 3,425,471 A | 2/1969 | Yates | |
| 3,511,241 A | 5/1970 | Lee | |
| 3,512,185 A * | 5/1970 | Ellis | A61F 5/455 4/144.3 |
| 3,520,300 A | 7/1970 | Flower | |
| 3,528,423 A | 9/1970 | Lee | |
| 3,613,123 A * | 10/1971 | Langstrom | A61F 5/4401 4/144.1 |
| 3,648,700 A | 3/1972 | Warner | |
| 3,651,810 A | 3/1972 | Ormerod | |
| 3,661,155 A | 5/1972 | Lindan | |
| 3,699,815 A | 10/1972 | Holbrook | |
| 3,726,277 A | 4/1973 | Hirschman | |
| 3,742,952 A | 7/1973 | Magers et al. | |
| 3,757,355 A | 9/1973 | Allen et al. | |
| 3,788,324 A | 1/1974 | Lim | |
| 3,843,016 A | 10/1974 | Bornhorst et al. | |
| 3,863,638 A | 2/1975 | Rogers et al. | |
| 3,863,798 A | 2/1975 | Kurihara et al. | |
| 3,864,759 A | 2/1975 | Horiuchi | |
| 3,881,486 A | 5/1975 | Fenton | |
| 3,915,189 A | 10/1975 | Holbrook et al. | |
| 3,998,228 A | 12/1976 | Poidomani | |
| 3,999,550 A | 12/1976 | Martin | |
| 4,015,604 A | 4/1977 | Csillag | |
| 4,020,843 A | 5/1977 | Kanall | |
| 4,022,213 A | 5/1977 | Stein | |
| 4,027,776 A | 6/1977 | Douglas | |
| 4,116,197 A | 9/1978 | Bermingham | |
| 4,180,178 A | 12/1979 | Turner | |
| 4,187,953 A | 2/1980 | Turner | |
| 4,194,508 A | 3/1980 | Anderson | |
| 4,200,102 A * | 4/1980 | Duhamel | A61F 5/451 604/353 |
| 4,202,058 A | 5/1980 | Anderson | |
| 4,233,025 A | 11/1980 | Larson et al. | |
| 4,233,978 A | 11/1980 | Hickey | |
| 4,246,901 A | 1/1981 | Frosch et al. | |
| 4,257,418 A * | 3/1981 | Hessner | A61F 5/4401 604/397 |
| 4,270,539 A * | 6/1981 | Frosch | A61F 5/455 604/347 |
| 4,281,655 A | 8/1981 | Terauchi | |
| 4,292,916 A | 10/1981 | Bradley et al. | |
| 4,352,356 A | 10/1982 | Tong | |
| 4,360,933 A | 11/1982 | Kimura et al. | |
| 4,365,363 A | 12/1982 | Windauer | |
| 4,387,726 A | 6/1983 | Denard | |
| 4,425,130 A | 1/1984 | Desmarais | |
| 4,446,986 A | 5/1984 | Bowen et al. | |
| 4,453,938 A | 6/1984 | Brendling | |
| 4,457,314 A | 7/1984 | Knowles | |
| 4,476,879 A | 10/1984 | Jackson | |
| 4,526,688 A | 7/1985 | Schmidt et al. | |
| 4,528,703 A | 7/1985 | Kraus | |
| D280,438 S | 9/1985 | Wendt | |
| 4,551,141 A | 11/1985 | McNeil | |
| 4,553,968 A | 11/1985 | Komis | |
| 4,581,026 A | 4/1986 | Schneider | |
| 4,610,675 A | 9/1986 | Triunfol | |
| 4,620,333 A | 11/1986 | Ritter | |
| 4,626,250 A | 12/1986 | Schneider | |
| 4,627,846 A | 12/1986 | Ternstroem | |
| 4,631,061 A * | 12/1986 | Martin | A61F 5/451 604/323 |
| 4,650,477 A | 3/1987 | Johnson | |
| 4,656,675 A | 4/1987 | Fajnsztajn | |
| 4,681,570 A | 7/1987 | Dalton | |
| 4,692,160 A | 9/1987 | Nussbaumer | |
| 4,707,864 A | 11/1987 | Ikematsu et al. | |
| 4,713,066 A | 12/1987 | Komis | |
| 4,747,166 A * | 5/1988 | Kuntz | A61F 5/455 4/144.1 |
| 4,752,944 A | 6/1988 | Conrads et al. | |
| 4,769,215 A | 9/1988 | Ehrenkranz | |
| 4,772,280 A | 9/1988 | Rooyakkers | |
| 4,790,830 A | 12/1988 | Hamacher | |
| 4,790,835 A | 12/1988 | Elias | |
| 4,791,686 A | 12/1988 | Taniguchi et al. | |
| 4,795,449 A * | 1/1989 | Schneider | A61F 5/4405 604/326 |
| 4,798,603 A | 1/1989 | Meyer et al. | |
| 4,799,928 A | 1/1989 | Crowley | |
| 4,804,377 A | 2/1989 | Hanifl et al. | |
| 4,812,053 A | 3/1989 | Bhattacharjee | |
| 4,820,297 A | 4/1989 | Kaufman et al. | |
| 4,846,818 A | 7/1989 | Keldahl et al. | |
| 4,846,909 A | 7/1989 | Klug et al. | |
| 4,865,595 A | 9/1989 | Heyden | |
| 4,882,794 A | 11/1989 | Stewart | |
| 4,883,465 A | 11/1989 | Brennan | |
| 4,886,508 A * | 12/1989 | Washington | A61F 5/455 604/347 |
| 4,886,509 A | 12/1989 | Mattsson | |
| 4,889,532 A | 12/1989 | Metz et al. | |
| 4,889,533 A | 12/1989 | Beecher | |
| 4,903,254 A | 2/1990 | Haas | |
| 4,905,692 A | 3/1990 | More | |
| 4,936,838 A | 6/1990 | Cross et al. | |
| 4,955,922 A | 9/1990 | Terauchi | |
| 4,957,487 A | 9/1990 | Gerow | |
| 4,965,460 A | 10/1990 | Tanaka et al. | |
| 4,987,849 A | 1/1991 | Sherman | |
| 5,002,541 A | 3/1991 | Conkling et al. | |
| 5,004,463 A | 4/1991 | Nigay | |
| 5,031,248 A | 7/1991 | Kemper | |
| 5,045,077 A | 9/1991 | Blake | |
| 5,045,283 A | 9/1991 | Patel | |
| 5,049,144 A * | 9/1991 | Payton | A61F 5/455 600/574 |
| 5,053,339 A | 10/1991 | Patel | |
| 5,058,088 A | 10/1991 | Haas et al. | |
| 5,071,347 A | 12/1991 | McGuire | |
| 5,078,707 A | 1/1992 | Peter | |
| 5,084,037 A | 1/1992 | Barnett | |
| 5,100,396 A | 3/1992 | Zamierowski | |
| 5,147,301 A | 9/1992 | Ruvio | |
| 5,195,997 A | 3/1993 | Carns | |
| 5,203,699 A | 4/1993 | McGuire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,294,983 A | 3/1994 | Ersoz et al. | |
| 5,295,983 A * | 3/1994 | Kubo | A61F 5/455 4/144.3 |
| 5,300,052 A | 4/1994 | Kubo | |
| 5,312,383 A | 5/1994 | Kubalak | |
| 5,318,550 A | 6/1994 | Cermak et al. | |
| 5,340,840 A | 8/1994 | Park et al. | |
| 5,382,244 A | 1/1995 | Telang | |
| 5,423,784 A | 6/1995 | Metz | |
| 5,466,229 A * | 11/1995 | Elson | A61M 1/78 604/323 |

(56) References Cited

U.S. PATENT DOCUMENTS

| | | | |
|---|---|---|---|
| 5,478,334 | A | 12/1995 | Bernstein |
| 5,499,977 | A | 3/1996 | Marx |
| 5,543,042 | A | 8/1996 | Filan et al. |
| D373,928 | S | 9/1996 | Green |
| 5,605,161 | A | 2/1997 | Cross |
| 5,618,277 | A | 4/1997 | Goulter |
| 5,628,735 | A | 5/1997 | Skow |
| 5,636,643 | A | 6/1997 | Argenta et al. |
| 5,637,104 | A | 6/1997 | Ball et al. |
| 5,674,212 | A * | 10/1997 | Osborn, III ............ A61F 13/15 604/385.16 |
| 5,678,564 | A * | 10/1997 | Lawrence ............... A61F 5/455 600/573 |
| 5,678,654 | A | 10/1997 | Uzawa |
| 5,687,429 | A | 11/1997 | Rahlff |
| 5,695,485 | A | 12/1997 | Duperret et al. |
| 5,752,944 | A | 5/1998 | Dann et al. |
| 5,772,644 | A | 6/1998 | Bark et al. |
| 5,792,132 | A | 8/1998 | Garcia |
| 5,827,243 | A | 10/1998 | Palestrant |
| 5,827,247 | A | 10/1998 | Kay |
| 5,827,250 | A | 10/1998 | Fujioka et al. |
| 5,827,257 | A | 10/1998 | Fujioka et al. |
| D401,699 | S | 11/1998 | Herchenbach et al. |
| 5,865,378 | A | 2/1999 | Hollinshead et al. |
| 5,887,291 | A | 3/1999 | Bellizzi |
| 5,894,608 | A * | 4/1999 | Birbara ................. A61F 5/4556 604/319 |
| D409,303 | S | 5/1999 | Oepping |
| 5,911,222 | A * | 6/1999 | Lawrence ............... A61F 5/455 600/573 |
| 5,957,904 | A | 9/1999 | Holland |
| 5,972,505 | A | 10/1999 | Phillips et al. |
| 6,050,983 | A | 4/2000 | Moore et al. |
| 6,059,762 | A | 5/2000 | Boyer et al. |
| 6,063,064 | A | 5/2000 | Tuckey et al. |
| 6,098,625 | A | 8/2000 | Winkler |
| 6,105,174 | A | 8/2000 | Karlsten et al. |
| 6,113,582 | A | 9/2000 | Dwork |
| 6,117,163 | A * | 9/2000 | Bierman ............... A61M 25/02 606/232 |
| 6,123,398 | A * | 9/2000 | Arai .................... B60T 8/17552 303/151 |
| 6,129,718 | A | 10/2000 | Wada et al. |
| 6,131,964 | A | 10/2000 | Sareshwala |
| 6,152,902 | A | 11/2000 | Christian et al. |
| 6,164,569 | A | 12/2000 | Hollinshead et al. |
| 6,177,606 | B1 | 1/2001 | Etheredge et al. |
| 6,209,142 | B1 | 4/2001 | Mattsson et al. |
| 6,248,096 | B1 | 6/2001 | Dwork et al. |
| 6,263,887 | B1 | 7/2001 | Dunn |
| 6,311,339 | B1 * | 11/2001 | Kraus ................... A61G 9/006 4/144.1 |
| 6,336,919 | B1 | 1/2002 | Davis et al. |
| 6,338,729 | B1 | 1/2002 | Wada et al. |
| 6,352,525 | B1 | 3/2002 | Wakabayashi |
| 6,394,988 | B1 | 5/2002 | Hashimoto |
| 6,406,463 | B1 | 6/2002 | Brown |
| 6,409,712 | B1 | 6/2002 | Dutari et al. |
| 6,416,500 | B1 | 7/2002 | Wada et al. |
| 6,428,521 | B1 | 8/2002 | Droll |
| 6,475,198 | B1 | 11/2002 | Lipman et al. |
| 6,479,726 | B1 | 11/2002 | Cole et al. |
| 6,491,673 | B1 | 12/2002 | Palumbo et al. |
| 6,508,794 | B1 | 1/2003 | Palumbo et al. |
| 6,540,729 | B1 | 4/2003 | Wada et al. |
| 6,547,771 | B2 | 4/2003 | Robertson et al. |
| 6,569,133 | B2 | 5/2003 | Cheng et al. |
| D476,518 | S | 7/2003 | Doppelt |
| 6,592,560 | B2 | 7/2003 | Snyder et al. |
| 6,618,868 | B2 | 9/2003 | Minnick |
| 6,620,142 | B1 | 9/2003 | Flueckiger |
| 6,629,651 | B1 | 10/2003 | Male et al. |
| 6,635,038 | B2 | 10/2003 | Scovel |
| 6,652,495 | B1 | 11/2003 | Walker |
| 6,685,684 | B1 | 2/2004 | Falconer |
| 6,702,793 | B1 | 3/2004 | Sweetser et al. |
| 6,706,027 | B2 * | 3/2004 | Harvie ................... A61F 5/455 604/326 |
| 6,732,384 | B2 * | 5/2004 | Scott .................... A47K 11/12 4/144.1 |
| 6,736,977 | B1 | 5/2004 | Hall et al. |
| 6,740,066 | B2 * | 5/2004 | Wolff ................... A61F 5/451 604/323 |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,849,065 | B2 | 2/2005 | Schmidt et al. |
| 6,857,137 | B2 | 2/2005 | Otto |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 * | 7/2005 | Harvie ................... A61F 5/451 604/326 |
| 6,979,324 | B2 | 12/2005 | Bybordi et al. |
| 7,018,366 | B2 * | 3/2006 | Easter ................... A61F 5/451 604/327 |
| 7,066,411 | B2 | 6/2006 | Male et al. |
| 7,122,023 | B1 | 10/2006 | Hinoki |
| 7,125,399 | B2 | 10/2006 | Miskie |
| 7,131,964 | B2 * | 11/2006 | Harvie ................... A61F 5/455 604/326 |
| 7,135,012 | B2 * | 11/2006 | Harvie ................... A61F 5/453 604/326 |
| 7,141,043 | B2 * | 11/2006 | Harvie ................... A61F 5/451 604/326 |
| D533,972 | S | 12/2006 | La Luzerne |
| 7,160,273 | B2 | 1/2007 | Greter et al. |
| 7,171,699 | B2 | 2/2007 | Ernest et al. |
| 7,171,871 | B2 | 2/2007 | Kozak |
| 7,179,951 | B2 | 2/2007 | Krishnaswamy-Mirle et al. |
| 7,181,781 | B1 * | 2/2007 | Trabold ................. A61F 5/455 4/144.1 |
| 7,186,245 | B1 | 3/2007 | Cheng et al. |
| 7,192,424 | B2 | 3/2007 | Cooper |
| 7,220,250 | B2 * | 5/2007 | Suzuki .................. A61F 5/451 604/328 |
| D562,975 | S | 2/2008 | Otto |
| 7,335,189 | B2 * | 2/2008 | Harvie ................... A61F 5/451 604/326 |
| 7,358,282 | B2 | 4/2008 | Krueger et al. |
| 7,390,320 | B2 * | 6/2008 | Machida ................ A61F 5/455 4/144.1 |
| 7,438,706 | B2 | 10/2008 | Koizumi et al. |
| 7,488,310 | B2 | 2/2009 | Yang |
| 7,491,194 | B1 | 2/2009 | Oliwa |
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,585,293 | B2 | 9/2009 | Vermaak |
| 7,588,560 | B1 | 9/2009 | Dunlop |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 * | 4/2010 | Bengtson .............. A61M 27/00 604/313 |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 * | 7/2010 | Tazoe ................... A61F 5/451 604/320 |
| 7,755,497 | B2 * | 7/2010 | Wada .................... A61F 5/451 340/604 |
| 7,766,887 | B2 | 8/2010 | Burns et al. |
| D625,407 | S | 10/2010 | Koizumi et al. |

(56) References Cited

U.S. PATENT DOCUMENTS

| | | | |
|---|---|---|---|
| 7,806,879 B2 | 10/2010 | Brooks et al. | |
| 7,811,272 B2 | 10/2010 | Lindsay et al. | |
| 7,815,067 B2 | 10/2010 | Matsumoto et al. | |
| 7,833,169 B2 | 11/2010 | Hannon | |
| 7,857,806 B2 | 12/2010 | Karpowicz et al. | |
| 7,866,942 B2 | 1/2011 | Harvie | |
| 7,871,385 B2 | 1/2011 | Levinson et al. | |
| 7,875,010 B2 | 1/2011 | Frazier et al. | |
| 7,901,389 B2 | 3/2011 | Mombrinie | |
| 7,927,320 B2 | 4/2011 | Goldwasser et al. | |
| 7,927,321 B2 | 4/2011 | Marland | |
| 7,931,634 B2 | 4/2011 | Swiecicki et al. | |
| 7,939,706 B2 | 5/2011 | Okabe et al. | |
| 7,946,443 B2 | 5/2011 | Stull et al. | |
| 7,947,025 B2 | 5/2011 | Buglino et al. | |
| 7,963,419 B2 | 6/2011 | Burney et al. | |
| 7,976,519 B2 | 7/2011 | Bubb et al. | |
| 7,993,318 B2 | 8/2011 | Olsson et al. | |
| 8,015,627 B2 | 9/2011 | Baker et al. | |
| 8,028,460 B2 | 10/2011 | Williams | |
| 8,047,398 B2 | 11/2011 | Dimartino et al. | |
| 8,083,094 B2 | 12/2011 | Caulfield et al. | |
| 8,128,608 B2 * | 3/2012 | Thevenin | A61F 13/84 604/347 |
| 8,181,651 B2 | 5/2012 | Pinel | |
| 8,181,819 B2 | 5/2012 | Burney et al. | |
| 8,211,063 B2 * | 7/2012 | Bierman | A61M 25/02 604/179 |
| 8,221,369 B2 | 7/2012 | Parks et al. | |
| 8,241,262 B2 | 8/2012 | Mahnensmith | |
| 8,277,426 B2 | 10/2012 | Wilcox et al. | |
| 8,287,508 B1 * | 10/2012 | Sanchez | A61F 5/4404 604/326 |
| 8,303,554 B2 | 11/2012 | Tsai et al. | |
| 8,322,565 B2 | 12/2012 | Caulfield et al. | |
| 8,337,477 B2 | 12/2012 | Parks et al. | |
| D674,241 S | 1/2013 | Bickert et al. | |
| 8,343,122 B2 | 1/2013 | Gorres | |
| 8,353,074 B2 | 1/2013 | Krebs | |
| 8,353,886 B2 | 1/2013 | Bester et al. | |
| D676,241 S | 2/2013 | Merrill | |
| 8,388,588 B2 | 3/2013 | Wada et al. | |
| D679,807 S | 4/2013 | Burgess et al. | |
| 8,425,482 B2 | 4/2013 | Khoubnazar | |
| 8,449,510 B2 | 5/2013 | Martini et al. | |
| D684,260 S | 6/2013 | Lund et al. | |
| 8,470,230 B2 | 6/2013 | Caulfield et al. | |
| 8,479,941 B2 | 7/2013 | Matsumoto et al. | |
| 8,479,949 B2 | 7/2013 | Henkel | |
| 8,512,301 B2 | 8/2013 | Ma | |
| 8,529,530 B2 | 9/2013 | Koch et al. | |
| 8,535,284 B2 | 9/2013 | Joder et al. | |
| 8,546,639 B2 * | 10/2013 | Wada | A61F 5/4401 604/361 |
| 8,551,075 B2 * | 10/2013 | Bengtson | A61M 1/84 604/543 |
| 8,568,376 B2 | 10/2013 | Delattre et al. | |
| D694,404 S | 11/2013 | Burgess et al. | |
| 8,585,683 B2 * | 11/2013 | Bengtson | A61M 1/985 604/543 |
| 8,586,583 B2 | 11/2013 | Hamblin et al. | |
| 8,652,112 B2 | 2/2014 | Johannison et al. | |
| D702,973 S | 4/2014 | Norland et al. | |
| 8,703,032 B2 | 4/2014 | Menon et al. | |
| D704,330 S | 5/2014 | Cicatelli | |
| D704,510 S | 5/2014 | Mason et al. | |
| D705,423 S | 5/2014 | Walsh Cutler | |
| D705,926 S | 5/2014 | Burgess et al. | |
| 8,714,394 B2 | 5/2014 | Wulf | |
| 8,715,267 B2 | 5/2014 | Bengtson et al. | |
| 8,757,425 B2 | 6/2014 | Copeland | |
| 8,777,032 B2 | 7/2014 | Biesecker et al. | |
| 8,808,260 B2 | 8/2014 | Koch et al. | |
| 8,864,730 B2 | 10/2014 | Conway et al. | |
| 8,881,923 B2 | 11/2014 | Higginson | |
| 8,936,585 B2 | 1/2015 | Carson et al. | |
| D729,581 S | 5/2015 | Boroski | |
| 9,028,460 B2 * | 5/2015 | Medeiros | A61F 5/451 604/347 |
| 9,056,698 B2 | 6/2015 | Noer | |
| 9,078,792 B2 | 7/2015 | Ruiz | |
| 9,173,602 B2 | 11/2015 | Gilbert | |
| 9,173,799 B2 * | 11/2015 | Tanimoto | A61F 5/453 |
| 9,187,220 B2 | 11/2015 | Biesecker et al. | |
| 9,199,772 B2 | 12/2015 | Krippendorf | |
| 9,233,020 B2 | 1/2016 | Matsumiya | |
| 9,248,058 B2 | 2/2016 | Conway et al. | |
| 9,308,118 B1 | 4/2016 | Dupree et al. | |
| 9,309,029 B2 | 4/2016 | Incorvia et al. | |
| 9,333,281 B2 | 5/2016 | Giezendanner et al. | |
| 9,382,047 B2 | 7/2016 | Schmidtner et al. | |
| 9,456,937 B2 | 10/2016 | Ellis | |
| 9,480,595 B2 | 11/2016 | Baham et al. | |
| 9,517,865 B2 | 12/2016 | Albers et al. | |
| D777,941 S | 1/2017 | Piramoon | |
| 9,533,806 B2 | 1/2017 | Ding et al. | |
| 9,550,611 B2 | 1/2017 | Hodge | |
| 9,555,930 B2 | 1/2017 | Campbell et al. | |
| D789,522 S | 6/2017 | Burgess et al. | |
| 9,687,849 B2 | 6/2017 | Bruno et al. | |
| 9,694,949 B2 | 7/2017 | Hendricks et al. | |
| 9,788,992 B2 | 10/2017 | Harvie | |
| D804,907 S | 12/2017 | Sandoval | |
| 9,868,564 B2 | 1/2018 | McGirr et al. | |
| D814,239 S | 4/2018 | Arora | |
| D817,484 S | 5/2018 | Lafond | |
| 10,037,640 B2 | 7/2018 | Gordon | |
| 10,058,470 B2 | 8/2018 | Phillips | |
| 10,098,990 B2 | 10/2018 | Koch et al. | |
| D835,264 S | 12/2018 | Mozzicato et al. | |
| D835,779 S | 12/2018 | Mozzicato et al. | |
| D840,533 S | 2/2019 | Mozzicato et al. | |
| D840,534 S | 2/2019 | Mozzicato et al. | |
| 10,225,376 B2 | 3/2019 | Perez Martinez | |
| 10,226,376 B2 * | 3/2019 | Sanchez | A61F 5/455 |
| D848,612 S | 5/2019 | Mozzicato et al. | |
| 10,307,305 B1 | 6/2019 | Hodges | |
| 10,335,121 B2 | 7/2019 | Desai | |
| D856,512 S | 8/2019 | Cowart et al. | |
| 10,376,406 B2 * | 8/2019 | Newton | A61F 5/4404 |
| 10,376,407 B2 | 8/2019 | Newton | |
| 10,390,989 B2 * | 8/2019 | Sanchez | A61F 5/453 |
| D858,144 S | 9/2019 | Fu | |
| 10,406,039 B2 | 9/2019 | Villarreal | |
| 10,407,222 B2 | 9/2019 | Allen | |
| 10,478,356 B2 | 11/2019 | Griffin | |
| 10,538,366 B2 | 1/2020 | Pentelovitch et al. | |
| 10,569,938 B2 | 2/2020 | Zhao et al. | |
| 10,577,156 B2 | 3/2020 | Dagnelie et al. | |
| 10,618,721 B2 | 4/2020 | Vazin | |
| D884,390 S | 5/2020 | Wang | |
| 10,669,079 B2 | 6/2020 | Freedman et al. | |
| D892,315 S | 8/2020 | Airy | |
| 10,730,672 B2 | 8/2020 | Bertram et al. | |
| 10,737,848 B2 | 8/2020 | Philip et al. | |
| 10,765,854 B2 | 9/2020 | Law et al. | |
| 10,766,670 B2 | 9/2020 | Kittmann | |
| D901,214 S | 11/2020 | Hu | |
| 10,857,025 B2 | 12/2020 | Davis et al. | |
| 10,865,017 B1 | 12/2020 | Cowart et al. | |
| 10,889,412 B2 | 1/2021 | West et al. | |
| 10,913,581 B2 | 2/2021 | Stahlecker | |
| D912,244 S | 3/2021 | Rehm et al. | |
| 10,952,889 B2 * | 3/2021 | Newton | A61F 5/4404 |
| 10,973,678 B2 * | 4/2021 | Newton | A61M 1/71 |
| 10,974,874 B2 | 4/2021 | Ragias et al. | |
| 11,000,401 B2 | 5/2021 | Ecklund et al. | |
| D923,365 S | 6/2021 | Wang | |
| 11,026,829 B2 * | 6/2021 | Harvie | A61M 25/0017 |
| 11,027,900 B2 | 6/2021 | Liu | |
| 11,045,346 B2 | 6/2021 | Argent et al. | |
| D928,946 S * | 8/2021 | Sanchez | D24/122 |
| 11,179,506 B2 | 11/2021 | Barr et al. | |

(56) References Cited

U.S. PATENT DOCUMENTS

| | | | |
|---|---|---|---|
| 11,226,376 B2 | 1/2022 | Yamauchi et al. | |
| 11,376,152 B2* | 7/2022 | Sanchez | A61F 5/4404 |
| 11,382,786 B2* | 7/2022 | Sanchez | A61F 5/455 |
| 11,382,788 B2 | 7/2022 | Hjorth et al. | |
| 11,426,303 B2* | 8/2022 | Davis | A61B 5/208 |
| 11,529,252 B2 | 12/2022 | Glithero et al. | |
| 2001/0037097 A1 | 11/2001 | Cheng et al. | |
| 2001/0054426 A1 | 12/2001 | Knudson et al. | |
| 2002/0019614 A1* | 2/2002 | Woon | A61F 13/53747 604/378 |
| 2002/0026161 A1 | 2/2002 | Grundke | |
| 2002/0087131 A1* | 7/2002 | Wolff | A61B 5/20 604/327 |
| 2002/0091364 A1 | 7/2002 | Prabhakar | |
| 2002/0189992 A1 | 12/2002 | Schmidt et al. | |
| 2002/0193760 A1 | 12/2002 | Thompson | |
| 2003/0004436 A1 | 1/2003 | Schmidt et al. | |
| 2003/0120178 A1 | 6/2003 | Heki | |
| 2003/0157859 A1 | 8/2003 | Ishikawa | |
| 2003/0181880 A1 | 9/2003 | Schwartz | |
| 2003/0195484 A1* | 10/2003 | Harvie | A61F 5/455 604/355 |
| 2003/0233079 A1 | 12/2003 | Parks et al. | |
| 2004/0006321 A1 | 1/2004 | Cheng et al. | |
| 2004/0056122 A1 | 3/2004 | Male et al. | |
| 2004/0084465 A1 | 5/2004 | Luburic | |
| 2004/0127872 A1* | 7/2004 | Petryk | A61F 13/49 604/382 |
| 2004/0128749 A1 | 7/2004 | Scott | |
| 2004/0143229 A1* | 7/2004 | Easter | A61F 5/451 604/322 |
| 2004/0147894 A1 | 7/2004 | Mizutani et al. | |
| 2004/0158221 A1 | 8/2004 | Mizutani et al. | |
| 2004/0176731 A1 | 9/2004 | Cheng et al. | |
| 2004/0191919 A1 | 9/2004 | Unger et al. | |
| 2004/0207530 A1* | 10/2004 | Nielsen | A61F 13/42 340/573.5 |
| 2004/0236292 A1* | 11/2004 | Tazoe | A61F 5/451 604/317 |
| 2004/0254547 A1* | 12/2004 | Okabe | A61F 5/455 604/317 |
| 2005/0010182 A1 | 1/2005 | Parks et al. | |
| 2005/0033248 A1* | 2/2005 | Machida | A61F 5/455 604/327 |
| 2005/0070861 A1* | 3/2005 | Okabe | A61F 5/4404 604/327 |
| 2005/0070862 A1* | 3/2005 | Tazoe | A61F 5/441 604/327 |
| 2005/0082300 A1 | 4/2005 | Modrell et al. | |
| 2005/0097662 A1 | 5/2005 | Leimkuhler et al. | |
| 2005/0101924 A1 | 5/2005 | Elson et al. | |
| 2005/0137557 A1 | 6/2005 | Swiecicki et al. | |
| 2005/0154360 A1 | 7/2005 | Harvie | |
| 2005/0177070 A1 | 8/2005 | Levinson et al. | |
| 2005/0197639 A1 | 9/2005 | Mombrinie | |
| 2005/0273920 A1 | 12/2005 | Marinas | |
| 2005/0277904 A1 | 12/2005 | Chase et al. | |
| 2005/0279359 A1 | 12/2005 | Leblanc et al. | |
| 2006/0004332 A1 | 1/2006 | Marx | |
| 2006/0015080 A1 | 1/2006 | Mahnensmith | |
| 2006/0015081 A1* | 1/2006 | Suzuki | A61F 5/451 604/329 |
| 2006/0016778 A1 | 1/2006 | Park | |
| 2006/0079854 A1 | 4/2006 | Kay et al. | |
| 2006/0111648 A1* | 5/2006 | Vermaak | A61B 10/007 604/355 |
| 2006/0155214 A1* | 7/2006 | Wightman | A61F 5/455 600/574 |
| 2006/0200102 A1 | 9/2006 | Cooper | |
| 2006/0229576 A1 | 10/2006 | Conway et al. | |
| 2006/0231648 A1 | 10/2006 | Male et al. | |
| 2006/0235359 A1 | 10/2006 | Marland | |
| 2006/0277670 A1 | 12/2006 | Baker et al. | |
| 2007/0006368 A1 | 1/2007 | Key et al. | |
| 2007/0038194 A1* | 2/2007 | Wada | A61F 5/451 604/347 |
| 2007/0055209 A1 | 3/2007 | Patel et al. | |
| 2007/0073252 A1 | 3/2007 | Forgrave | |
| 2007/0117880 A1 | 5/2007 | Elson et al. | |
| 2007/0135786 A1 | 6/2007 | Schmidt et al. | |
| 2007/0149935 A1 | 6/2007 | Dirico | |
| 2007/0191804 A1 | 8/2007 | Coley | |
| 2007/0214553 A1* | 9/2007 | Carromba | A47K 11/12 4/144.4 |
| 2007/0225666 A1 | 9/2007 | Otto | |
| 2007/0225668 A1 | 9/2007 | Otto | |
| 2007/0266486 A1 | 11/2007 | Ramirez | |
| 2007/0282309 A1 | 12/2007 | Bengtson et al. | |
| 2008/0004576 A1 | 1/2008 | Tanaka et al. | |
| 2008/0015526 A1 | 1/2008 | Reiner et al. | |
| 2008/0015527 A1 | 1/2008 | House | |
| 2008/0033386 A1* | 2/2008 | Okabe | A61F 5/4404 604/378 |
| 2008/0041869 A1 | 2/2008 | Backaert | |
| 2008/0091153 A1* | 4/2008 | Harvie | A61F 5/451 604/318 |
| 2008/0091158 A1 | 4/2008 | Yang | |
| 2008/0183157 A1 | 7/2008 | Walters | |
| 2008/0215031 A1 | 9/2008 | Belfort et al. | |
| 2008/0234642 A1 | 9/2008 | Patterson et al. | |
| 2008/0281282 A1 | 11/2008 | Finger et al. | |
| 2008/0287894 A1* | 11/2008 | Van Den Heuvel | A61F 5/455 604/327 |
| 2009/0025717 A1 | 1/2009 | Pinel | |
| 2009/0048570 A1 | 2/2009 | Jensen | |
| 2009/0056003 A1 | 3/2009 | Ivie et al. | |
| 2009/0069761 A1 | 3/2009 | Vogel | |
| 2009/0069765 A1 | 3/2009 | Wortham | |
| 2009/0192482 A1* | 7/2009 | Dodge, II | A61F 13/53708 524/436 |
| 2009/0234312 A1 | 9/2009 | O'Toole et al. | |
| 2009/0251510 A1 | 10/2009 | Noro et al. | |
| 2009/0264840 A1 | 10/2009 | Virginio | |
| 2009/0270822 A1* | 10/2009 | Medeiros | A61F 5/451 604/347 |
| 2009/0281510 A1 | 11/2009 | Fisher | |
| 2010/0004612 A1* | 1/2010 | Thevenin | A61F 13/84 4/443 |
| 2010/0058660 A1 | 3/2010 | Williams | |
| 2010/0121289 A1 | 5/2010 | Parks et al. | |
| 2010/0158168 A1 | 6/2010 | Murthy et al. | |
| 2010/0185168 A1* | 7/2010 | Graauw | A61F 5/4556 604/347 |
| 2010/0198172 A1 | 8/2010 | Wada et al. | |
| 2010/0211032 A1* | 8/2010 | Tsai | A61F 5/453 604/319 |
| 2010/0234820 A1 | 9/2010 | Tsai et al. | |
| 2010/0241104 A1 | 9/2010 | Gilbert | |
| 2010/0263113 A1 | 10/2010 | Shelton et al. | |
| 2010/0310845 A1 | 12/2010 | Bond et al. | |
| 2011/0028922 A1 | 2/2011 | Kay et al. | |
| 2011/0034889 A1 | 2/2011 | Smith | |
| 2011/0036837 A1 | 2/2011 | Shang | |
| 2011/0040267 A1* | 2/2011 | Wada | A61F 5/4401 604/318 |
| 2011/0040271 A1* | 2/2011 | Rogers | A61F 5/4556 604/346 |
| 2011/0054426 A1 | 3/2011 | Stewart et al. | |
| 2011/0060300 A1* | 3/2011 | Weig | A61F 5/451 604/319 |
| 2011/0077495 A1 | 3/2011 | Gilbert | |
| 2011/0077606 A1 | 3/2011 | Wilcox et al. | |
| 2011/0087337 A1 | 4/2011 | Forsell | |
| 2011/0137273 A1 | 6/2011 | Muellejans et al. | |
| 2011/0145993 A1 | 6/2011 | Rader et al. | |
| 2011/0152802 A1 | 6/2011 | DiCamillo et al. | |
| 2011/0164147 A1 | 7/2011 | Takahashi et al. | |
| 2011/0172620 A1 | 7/2011 | Khambatta | |
| 2011/0172625 A1* | 7/2011 | Wada | A61F 13/42 604/385.01 |
| 2011/0202024 A1 | 8/2011 | Cozzens | |
| 2011/0238023 A1 | 9/2011 | Slayton | |

(56) References Cited

U.S. PATENT DOCUMENTS

| | | |
|---|---|---|
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1* | 5/2012 | Wheaton .............. A61F 5/453 |
| | | 128/885 |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1* | 8/2012 | Anzivino, Sr. ....... A61F 5/4556 |
| | | 4/144.3 |
| 2012/0233761 A1 | 9/2012 | Huang |
| 2012/0245542 A1* | 9/2012 | Suzuki .................. A61F 13/84 |
| | | 374/45 |
| 2012/0245547 A1 | 9/2012 | Wilcox et al. |
| 2012/0253303 A1* | 10/2012 | Suzuki .................. A61F 13/42 |
| | | 374/45 |
| 2012/0271259 A1 | 10/2012 | Ulert |
| 2012/0296305 A1 | 11/2012 | Barraza Khaled et al. |
| 2012/0330256 A1 | 12/2012 | Wilcox et al. |
| 2013/0006206 A1* | 1/2013 | Wada .................. A61F 13/535 |
| | | 604/385.01 |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0245496 A1 | 9/2013 | Wells et al. |
| 2013/0245586 A1 | 9/2013 | Jha |
| 2013/0292537 A1 | 11/2013 | Dirico |
| 2014/0031774 A1* | 1/2014 | Bengtson .............. A61M 1/90 |
| | | 604/319 |
| 2014/0157499 A1 | 6/2014 | Suzuki et al. |
| 2014/0182051 A1* | 7/2014 | Tanimoto .............. A61G 9/006 |
| | | 4/144.3 |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0359660 A1* | 12/2015 | Harvie .................. A61F 5/441 |
| | | 604/351 |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1* | 4/2016 | Timm .................. A61F 13/84 |
| | | 604/385.01 |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1* | 12/2016 | Newton .............. A01K 23/005 |
| 2016/0367411 A1 | 12/2016 | Justiz et al. |
| 2016/0367726 A1 | 12/2016 | Gratzer |
| 2016/0374848 A1* | 12/2016 | Sanchez .............. A61F 5/453 |
| | | 604/319 |
| 2017/0007438 A1* | 1/2017 | Harvie .............. A61F 5/453 |
| 2017/0100276 A1 | 4/2017 | Joh |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1* | 9/2017 | Sanchez .............. A61F 5/4404 |
| 2017/0266658 A1 | 9/2017 | Bruno et al. |
| 2017/0281399 A1* | 10/2017 | VanMiddendorp ..... A61F 5/455 |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0342748 A1 | 12/2017 | Griffin |
| 2017/0348139 A1* | 12/2017 | Newton .............. A61F 5/4404 |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0028349 A1* | 2/2018 | Newton .............. A61F 5/453 |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1* | 8/2018 | Davis .............. A61F 5/455 |
| 2018/0256384 A1 | 9/2018 | Kasirye |
| 2018/0271694 A1 | 9/2018 | Fernandez et al. |
| 2019/0001030 A1 | 1/2019 | Braga et al. |
| 2019/0021899 A1 | 1/2019 | Vlet |
| 2019/0038451 A1* | 2/2019 | Harvie .............. A61F 5/441 |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1* | 5/2019 | Sanchez .............. A61F 5/4404 |
| | | 604/319 |
| 2019/0224036 A1* | 7/2019 | Sanchez .............. A61F 5/443 |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1* | 10/2019 | Sanchez .............. A61F 5/453 |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0030595 A1 | 1/2020 | Boukidjian et al. |
| 2020/0046544 A1* | 2/2020 | Godinez .............. A61F 5/451 |
| 2020/0055638 A1 | 2/2020 | Lau et al. |
| 2020/0070392 A1 | 3/2020 | Huber et al. |
| 2020/0085610 A1 | 3/2020 | Cohn et al. |
| 2020/0086090 A1 | 3/2020 | Von Weymarn-Schärli et al. |
| 2020/0129322 A1 | 4/2020 | Leuckel |
| 2020/0171217 A9 | 6/2020 | Braga et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315838 A1 | 10/2020 | Eckert |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0385179 A1 | 12/2020 | McCourt |
| 2020/0390591 A1 | 12/2020 | Glithero et al. |

(56) References Cited

U.S. PATENT DOCUMENTS

| | | | |
|---|---|---|---|
| 2020/0390592 A1 | 12/2020 | Merrill | |
| 2020/0405521 A1 | 12/2020 | Glasroe | |
| 2021/0008771 A1 | 1/2021 | Huber et al. | |
| 2021/0009323 A1 | 1/2021 | Markarian et al. | |
| 2021/0061523 A1 | 3/2021 | Bytheway | |
| 2021/0069005 A1* | 3/2021 | Sanchez | A61F 5/443 |
| 2021/0069008 A1 | 3/2021 | Blabas et al. | |
| 2021/0113749 A1 | 4/2021 | Radl et al. | |
| 2021/0121318 A1 | 4/2021 | Pinlac | |
| 2021/0137724 A1 | 5/2021 | Ecklund et al. | |
| 2021/0154055 A1 | 5/2021 | Villarreal | |
| 2021/0170079 A1 | 6/2021 | Radl et al. | |
| 2021/0220162 A1 | 7/2021 | Jamison | |
| 2021/0220163 A1 | 7/2021 | Mayrand | |
| 2021/0228400 A1 | 7/2021 | Glithero | |
| 2021/0228401 A1 | 7/2021 | Becker et al. | |
| 2021/0228795 A1* | 7/2021 | Hughett | A61F 5/453 |
| 2021/0229877 A1 | 7/2021 | Ragias et al. | |
| 2021/0236323 A1* | 8/2021 | Austermann | A61F 5/453 |
| 2021/0267787 A1 | 9/2021 | Nazemi | |
| 2021/0315727 A1 | 10/2021 | Jiang | |
| 2021/0353450 A1 | 11/2021 | Sharma et al. | |
| 2021/0361469 A1 | 11/2021 | Liu et al. | |
| 2021/0369495 A1* | 12/2021 | Cheng | A61F 5/4405 |
| 2021/0386925 A1 | 12/2021 | Hartwell et al. | |
| 2021/0393433 A1 | 12/2021 | Godinez et al. | |
| 2022/0023091 A1 | 1/2022 | Ecklund et al. | |
| 2022/0047410 A1 | 2/2022 | Walthall | |
| 2022/0062027 A1 | 3/2022 | Mitchell et al. | |
| 2022/0062029 A1* | 3/2022 | Johannes | A61F 5/4401 |
| 2022/0066825 A1 | 3/2022 | Saraf et al. | |
| 2022/0071811 A1 | 3/2022 | Cheng et al. | |
| 2022/0104965 A1 | 4/2022 | Vaninetti et al. | |
| 2022/0104981 A1 | 4/2022 | Jones | |
| 2022/0117774 A1 | 4/2022 | Meyer et al. | |
| 2022/0117775 A1* | 4/2022 | Jones | A61L 26/0085 |
| 2022/0133524 A1* | 5/2022 | Davis | A61M 1/80 604/319 |
| 2022/0151817 A1 | 5/2022 | Mann | |
| 2022/0218510 A1 | 7/2022 | Metzger et al. | |
| 2022/0229053 A1 | 7/2022 | Levin et al. | |
| 2022/0248836 A1 | 8/2022 | Cagle et al. | |
| 2022/0257407 A1* | 8/2022 | Johannes | A61F 5/453 |
| 2022/0265462 A1* | 8/2022 | Alder | A61F 5/4404 |
| 2022/0273482 A1 | 9/2022 | Johannes et al. | |
| 2022/0280357 A1* | 9/2022 | Jagannathan | A61F 13/84 |
| 2022/0313474 A1 | 10/2022 | Kriscovich et al. | |
| 2022/0354685 A1 | 11/2022 | Davis et al. | |
| 2022/0370231 A1 | 11/2022 | Wang et al. | |
| 2022/0370234 A1* | 11/2022 | Hughett | A61F 5/451 |
| 2022/0370237 A1 | 11/2022 | Parmar et al. | |
| 2022/0387001 A1 | 12/2022 | Askenazi et al. | |
| 2022/0395391 A1* | 12/2022 | Saunders | A61F 5/4404 |
| 2023/0018845 A1* | 1/2023 | Lee | A61F 13/4752 |
| 2023/0020563 A1 | 1/2023 | Sharma et al. | |
| 2023/0037159 A1* | 2/2023 | Brennan | A61F 5/451 |
| 2023/0062944 A1 | 3/2023 | Vollenberg et al. | |
| 2023/0062994 A1 | 3/2023 | Ecklund et al. | |
| 2023/0089032 A1* | 3/2023 | Hughett | A61F 5/4404 |
| 2023/0105001 A1 | 4/2023 | Whittome et al. | |
| 2023/0138269 A1* | 5/2023 | Abdelal | A61F 5/451 604/347 |
| 2023/0145365 A1 | 5/2023 | Martin et al. | |

FOREIGN PATENT DOCUMENTS

| | | |
|---|---|---|
| CA | 2354132 A1 | 6/2000 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1533755 A | 10/2004 |
| CN | 1602825 A | 4/2005 |
| CN | 1720888 A | 1/2006 |
| CN | 2936204 Y | 8/2007 |
| CN | 101262836 A | 9/2008 |
| CN | 102159159 A | 8/2011 |
| CN | 202184840 U | 4/2012 |
| CN | 102481441 A | 5/2012 |
| CN | 103533968 A | 1/2014 |
| CN | 103717180 A | 4/2014 |
| CN | 204562697 U | 8/2015 |
| CN | 105451693 A | 3/2016 |
| CN | 205849719 U | 1/2017 |
| CN | 107847384 A | 3/2018 |
| CN | 107920912 A | 4/2018 |
| CN | 209285902 U | 8/2019 |
| CN | 211198839 U | 8/2020 |
| CN | 116096332 A | 5/2023 |
| DE | 79818 C | 10/1893 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 19619597 A1 | 11/1997 |
| DE | 102011103783 A1 | 12/2012 |
| DE | 202015104597 U1 | 7/2016 |
| DK | 9600118 | 11/1996 |
| EP | 0032138 A2 | 7/1981 |
| EP | 0066070 B1 | 12/1982 |
| EP | 0119143 B1 | 11/1988 |
| EP | 0610638 A1 | 8/1994 |
| EP | 0613355 A1 | 9/1994 |
| EP | 0613355 B1 | 1/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3788992 A1 | 3/2021 |
| EP | 3576689 B1 | 3/2022 |
| EP | 3752110 B1 | 3/2022 |
| EP | 4025163 A1 | 7/2022 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| IT | 201800009129 A1 | 4/2020 |
| JP | S5410596 A | 1/1979 |
| JP | S5410596 Y2 | 5/1979 |
| JP | S55155618 A | 12/1980 |
| JP | S5888596 U | 6/1983 |
| JP | S63107780 U | 7/1988 |
| JP | H0267530 A | 3/1990 |
| JP | H02103871 A | 4/1990 |
| JP | H02131422 A | 5/1990 |

(56) References Cited

FOREIGN PATENT DOCUMENTS

| | | |
|---|---|---|
| JP | H0460220 A | 2/1992 |
| JP | H05123349 A | 5/1993 |
| JP | H05123350 A | 5/1993 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2001054531 A | 2/2001 |
| JP | 2001070331 A | 3/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 3132659 B2 | 5/2007 |
| JP | 4039641 B2 | 11/2007 |
| JP | 2009509570 A | 3/2009 |
| JP | 2010081981 A | 4/2010 |
| JP | 4640772 B2 | 12/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2019525811 A | 9/2019 |
| JP | 2021120686 A | 8/2021 |
| KR | 200290061 Y1 | 9/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001846 A1 | 1/2017 |
| WO | 2017075226 A1 | 5/2017 |
| WO | 2017152198 A1 | 9/2017 |
| WO | 2017162559 A1 | 9/2017 |

(56) References Cited

FOREIGN PATENT DOCUMENTS

| | | |
|---|---|---|
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021094352 A1 | 5/2021 |
| WO | 2021102296 A1 | 5/2021 |
| WO | 2021138411 A1 | 7/2021 |
| WO | 2021138414 A1 | 7/2021 |
| WO | 2021155206 A1 | 8/2021 |
| WO | 2021173436 A1 | 9/2021 |
| WO | 2021195384 A1 | 9/2021 |
| WO | 2021207621 A1 | 10/2021 |
| WO | 2021211568 A1 | 10/2021 |
| WO | 2021216419 A1 | 10/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022076427 A2 | 4/2022 |
| WO | 2022086898 A1 | 4/2022 |
| WO | 2022098536 A1 | 5/2022 |
| WO | 2022125685 A1 | 6/2022 |
| WO | 2022140545 A1 | 6/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022192188 A1 | 9/2022 |
| WO | 2022192347 A1 | 9/2022 |
| WO | 2023038945 A1 | 3/2023 |
| WO | 2023038950 A1 | 3/2023 |

OTHER PUBLICATIONS

Advisory Action for U.S. Appl. No. 16/904,868 dated Jun. 15, 2022.
Final Office Action for U.S. Appl. No. 16/452,258 dated Jun. 14, 2022.
Final Office Action for U.S. Appl. No. 16/478,180 dated Jun. 22, 2022.
International Search Report and Written Opinion from International Application No. PCT/US2021/051456 dated Jan. 19, 2022.
International Search Report and Written Opinion from International Application No. PCT/US2021/055515 dated Jan. 28, 2022.
International Search Report and Written Opinion from International Application No. PCT/US2022/011419 dated Jun. 7, 2022.
International Search Report and Written Opinion from International Application No. PCT/US2022/012794 dated May 3, 2022.
International Search Report and Written Opinion from International Application No. PCT/US2022/015471 dated May 16, 2022.
International Search Report and Written Opinion from International Application No. PCT/US2022/016942 dated Jun. 8, 2022.
International Search Report and Written Opinion from International Application No. PCT/US2022/018170 dated May 31, 2022.
International Search Report and Written Opinion from International Application No. PCT/US2022/019254 dated Jun. 7, 2022.
Issue Notification for U.S. Appl. No. 17/088,272 dated Jun. 15, 2022.
Issue Notification for U.S. Appl. No. 17/330,657 dated Jun. 22, 2022.
Notice of Allowance for U.S. Appl. No. 29/741,751 dated Jun. 9, 2022.
U.S. Appl. No. 14/433,773, filed Apr. 3, 2020.
U.S. Appl. No. 17/664,914, filed May 25, 222.
U.S. Appl. No. 17/749,340, filed May 20, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 63/191,558, filed May 21, 2021.
Advisory Action for U.S. Appl. No. 14/722,613 dated Mar. 4, 2019.
Advisory Action for U.S. Appl. No. 14/952,591 dated Jun. 1, 2018.
Advisory Action for U.S. Appl. No. 15/238,427 dated Apr. 10, 2019.
Advisory Action for U.S. Appl. No. 16/899,956 dated Jul. 9, 2021.
Advisory Action for U.S. Appl. No. 16/904,868 dated Jul. 2, 2021.
Advisory Action for U.S. Appl. No. 16/905,400 dated Feb. 16, 2022.
Advisory Action for U.S. Appl. No. 16/905,400 dated Jun. 9, 2021.
Corrected International Search Report and Written Opinion for International Application No. PCT/US2017/043025 dated Jan. 11, 2018.
Corrected Notice of Allowability for U.S. Appl. No. 15/221,106 dated Jul. 2, 2019.
Corrected Notice of Allowability for U.S. Appl. No. 15/612,325 dated Mar. 17, 2021.
Corrected Notice of Allowability for U.S. Appl. No. 17/330,657 dated Dec. 9, 2021.
Final Office Action for U.S. Appl. No. 14/722,613 dated Nov. 29, 2018.
Final Office Action for U.S. Appl. No. 14/947,759 dated Apr. 8, 2016.
Final Office Action for U.S. Appl. No. 14/952,591 dated Feb. 23, 2018.
Final Office Action for U.S. Appl. No. 14/952,591 dated Nov. 1, 2019.
Final Office Action for U.S. Appl. No. 14/952,591 dated Nov. 27, 2020.
Final Office Action for U.S. Appl. No. 15/171,968 dated Feb. 14, 2020.

(56) References Cited

OTHER PUBLICATIONS

Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Final Office Action for U.S. Appl. No. 15/612,325 dated Sep. 17, 2020.
Final Office Action for U.S. Appl. No. 16/452,145 dated Mar. 25, 2022.
Final Office Action for U.S. Appl. No. 16/899,956 dated Apr. 19, 2021.
Final Office Action for U.S. Appl. No. 16/904,868 dated Mar. 10, 2022.
Final Office Action for U.S. Appl. No. 16/904,868 dated Mar. 26, 2021.
Final Office Action for U.S. Appl. No. 16/905,400 dated Apr. 6, 2021.
Final Office Action for U.S. Appl. No. 16/905,400 dated Dec. 9, 2021.
Final Office Action for U.S. Appl. No. 17/088,272 dated May 25, 2021.
Final Office Action for U.S. Appl. No. 29/624,661 dated Feb. 18, 2020.
International Search Report and Written Opinion from International Application No. PCT/US2016/049274 dated Dec. 1, 2016.
International Search Report and Written Opinion from International Application No. PCT/US2017/035625 dated Aug. 15, 2017.
International Search Report and Written Opinion from International Application No. PCT/US2017/043025 dated Oct. 18, 2017.
International Search Report and Written Opinion from International Application No. PCT/US2018/015968 dated Apr. 6, 2018.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
International Search Report and Written Opinion from International Application No. PCT/US2020/023572 dated Jul. 6, 2020.
International Search Report and Written Opinion from International Application No. PCT/US2020/033064 dated Aug. 31, 2020.
International Search Report and Written Opinion from International Application No. PCT/US2020/033122 dated Aug. 31, 2020.
International Search Report and Written Opinion from International Application No. PCT/US2020/040860 dated Oct. 2, 2020.
International Search Report and Written Opinion from International Application No. PCT/US2020/041242 dated Nov. 17, 2020.
International Search Report and Written Opinion from International Application No. PCT/US2020/041249 dated Oct. 2, 2020.
International Search Report and Written Opinion from International Application No. PCT/US2020/042262 dated Oct. 14, 2020.
International Search Report and Written Opinion from International Application No. PCT/US2020/043059 dated Oct. 6, 2020.
International Search Report and Written Opinion from International Application No. PCT/US2020/044024 dated Nov. 12, 2020.
International Search Report and Written Opinion from International Application No. PCT/US2020/046914 dated Dec. 1, 2020.
International Search Report and Written Opinion from International Application No. PCT/US2020/055680 dated Dec. 15, 2020.
International Search Report and Written Opinion from International Application No. PCT/US2020/057562 dated Jan. 27, 2021.
International Search Report and Written Opinion from International Application No. PCT/US2020/061563 dated Feb. 19, 2021.
International Search Report and Written Opinion from International Application No. PCT/US2020/065234 dated Apr. 12, 2021.
International Search Report and Written Opinion from International Application No. PCT/US2020/067451 dated Mar. 25, 2021.
International Search Report and Written Opinion from International Application No. PCT/US2020/067454 dated Mar. 29, 2021.
International Search Report and Written Opinion from International Application No. PCT/US2020/067455 dated Mar. 26, 2021.
International Search Report and Written Opinion from International Application No. PCT/US2021/015024 dated May 18, 2021.
International Search Report and Written Opinion from International Application No. PCT/US2021/015787 dated May 27, 2021.
International Search Report and Written Opinion from International Application No. PCT/US2021/023001 dated Jun. 21, 2021.
International Search Report and Written Opinion from International Application No. PCT/US2021/024162 dated Jul. 8, 2021.
International Search Report and Written Opinion from International Application No. PCT/US2021/026607 dated Jul. 29, 2021.
International Search Report and Written Opinion from International Application No. PCT/US2021/027061 dated Jul. 19, 2021.
International Search Report and Written Opinion from International Application No. PCT/US2021/027104 dated Jul. 6, 2021.
International Search Report and Written Opinion from International Application No. PCT/US2021/027314 dated Jul. 6, 2021.
International Search Report and Written Opinion from International Application No. PCT/US2021/027422 dated Aug. 12, 2021.
International Search Report and Written Opinion from International Application No. PCT/US2021/027425 dated Aug. 11, 2021.
International Search Report and Written Opinion from International Application No. PCT/US2021/027913 dated Jul. 12, 2021.
International Search Report and Written Opinion from International Application No. PCT/US2021/027917 dated Aug. 19, 2021.
International Search Report and Written Opinion from International Application No. PCT/US2021/035181 dated Sep. 16, 2021.
International Search Report and Written Opinion from International Application No. PCT/US2021/043893 dated Nov. 22, 2021.
International Search Report and Written Opinion from International Application No. PCT/US2021/044699 dated Nov. 22, 2021.
International Search Report and Written Opinion from International Application No. PCT/US2021/045188 dated Jan. 26, 2022.
International Search Report and Written Opinion from International Application No. PCT/US2021/047536 dated Dec. 23, 2021.
International Search Report and Written Opinion from International Application No. PCT/US2021/048211 dated Dec. 22, 2021.
International Search Report and Written Opinion from International Application No. PCT/US2021/048661 dated Feb. 14, 2022.
International Search Report and Written Opinion from International Application No. PCT/US2021/049404 dated Jan. 18, 2022.
International Search Report and Written Opinion from International Application No. PCT/US2021/053593 dated Apr. 11, 2022.
International Search Report and Written Opinion from International Application No. PCT/US2021/056566 dated Feb. 11, 2022.
International Search Report and Written Opinion from International Application No. PCT/US2021/060993 dated Mar. 18, 2022.
International Search Report and Written Opinion from International Application No. PCT/US2021/062440 dated Mar. 28, 2022.
International Search Report and Written Opinion from International Application No. PCT/US2022/011108 dated Apr. 22, 2022.
International Search Report and Written Opinion from International Application No. PCT/US2022/011281 dated Apr. 25, 2022.
Issue Notification for U.S. Appl. No. 14/952,591 dated Jul. 28, 2021.
Issue Notification for U.S. Appl. No. 15/171,968 dated Mar. 3, 2021.
Issue Notification for U.S. Appl. No. 15/221,106 dated Jul. 24, 2019.
Issue Notification for U.S. Appl. No. 15/238,427 dated Jul. 24, 2019.

(56) References Cited

OTHER PUBLICATIONS

Issue Notification for U.S. Appl. No. 15/260,103 dated Aug. 7, 2019.
Issue Notification for U.S. Appl. No. 15/611,587 dated Feb. 20, 2019.
Issue Notification for U.S. Appl. No. 15/612,325 dated Mar. 24, 2021.
Issue Notification for U.S. Appl. No. 29/624,661 dated Aug. 4, 2021.
Non-Final Office Action for U.S. Appl. No. 14/592,591 dated Mar. 20, 2020.
Non-Final Office Action for U.S. Appl. No. 14/722,613 dated Jun. 13, 2019.
Non-Final Office Action for U.S. Appl. No. 14/947,759 dated Mar. 17, 2016.
Non-Final Office Action for U.S. Appl. No. 14/952,591 dated Aug. 1, 2017.
Non-Final Office Action for U.S. Appl. No. 14/952,591 dated Mar. 20, 2020.
Non-Final Office Action for U.S. Appl. No. 14/952,591 dated Mar. 21, 2019.
Non-Final Office Action for U.S. Appl. No. 14/952,591 dated Sep. 28, 2018.
Non-Final Office Action for U.S. Appl. No. 15/171,968 dated May 11, 2020.
Non-Final Office Action for U.S. Appl. No. 15/171,968 dated Aug. 20, 2019.
Non-Final Office Action for U.S. Appl. No. 15/171,968 dated Jun. 12, 2018.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Dec. 29, 2017.
Non-Final Office Action for U.S. Appl. No. 15/611,587 dated Jul. 13, 2018.
Non-Final Office Action for U.S. Appl. No. 15/612,325 dated Mar. 19, 2020.
Non-Final Office Action for U.S. Appl. No. 16/245,726 dated Jan. 21, 2022.
Non-Final Office Action for U.S. Appl. No. 16/369,676 dated Mar. 31, 2022.
Non-Final Office Action for U.S. Appl. No. 16/433,773 dated Apr. 21, 2022.
Non-Final Office Action for U.S. Appl. No. 16/449,039 dated Dec. 8, 2021.
Non-Final Office Action for U.S. Appl. No. 16/452,145 dated Sep. 28, 2021.
Non-Final Office Action for U.S. Appl. No. 16/452,258 dated Sep. 28, 2021.
Non-Final Office Action for U.S. Appl. No. 16/478,180 dated Oct. 22, 2021.
Non-Final Office Action for U.S. Appl. No. 16/899,956 dated Oct. 16, 2020.
Non-Final Office Action for U.S. Appl. No. 16/899,956 dated Sep. 2, 2021.
Non-Final Office Action for U.S. Appl. No. 16/904,868 dated Nov. 25, 2020.
Non-Final Office Action for U.S. Appl. No. 16/904,868 dated Oct. 5, 2021.
Non-Final Office Action for U.S. Appl. No. 16/905,400 dated Apr. 27, 2022.
Non-Final Office Action for U.S. Appl. No. 16/905,400 dated Dec. 2, 2020.
Non-Final Office Action for U.S. Appl. No. 16/905,400 dated Jul. 22, 2021.
Non-Final Office Action for U.S. Appl. No. 17/088,272 dated Jan. 25, 2021.
Non-Final Office Action for U.S. Appl. No. 17/330,657 dated Aug. 11, 2021.
Non-Final Office Action for U.S. Appl. No. 29/624,661 dated Jul. 18, 2019.
Non-Final Office Action for U.S. Appl. No. 29/694,002 dated Jun. 24, 2020.
Non-Final Office Action for U.S. Appl. No. 29/741,751 dated Jan. 18, 2022.
Notice of Allowance for U.S. Appl. No. 14/952,591 dated Apr. 5, 2021.
Notice of Allowance for U.S. Appl. No. 14/952,591 dated Jul. 8, 2021.
Notice of Allowance for U.S. Appl. No. 15/171,968 dated Feb. 16, 2021.
Notice of Allowance for U.S. Appl. No. 15/171,968 dated Nov. 6, 2020.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
Notice of Allowance for U.S. Appl. No. 15/612,325 dated Feb. 19, 2021.
Notice of Allowance for U.S. Appl. No. 15/612,325 dated Jan. 21, 2021.
Notice of Allowance for U.S. Appl. No. 16/899,956 dated Apr. 19, 2022.
Notice of Allowance for U.S. Appl. No. 16/899,956 dated Dec. 29, 2021.
Notice of Allowance for U.S. Appl. No. 17/088,272 dated Aug. 5, 2021.
Notice of Allowance for U.S. Appl. No. 17/088,272 dated Mar. 4, 2022.
Notice of Allowance for U.S. Appl. No. 17/088,272 dated Nov. 24, 2021.
Notice of Allowance for U.S. Appl. No. 17/330,657 dated Mar. 16, 2022.
Notice of Allowance for U.S. Appl. No. 17/330,657 dated Nov. 26, 2021.
Notice of Allowance for U.S. Appl. No. 29/624,661 dated Apr. 28, 2021.
Notice of Allowance for U.S. Appl. No. 29/624,661 dated Jul. 10, 2020.
Notice of Allowance for U.S. Appl. No. 29/624,661 dated May 14, 2020.
Notice of Allowance for U.S. Appl. No. 29/624,661 dated Sep. 29, 2020.
Notice of Allowance for U.S. Appl. No. 29/694,002 dated Apr. 29, 2021.
Notice of Allowance for U.S. Appl. No. 29/694,002 dated Jan. 29, 2021.
Notice of Allowance for U.S. Appl. No. 29/694,002 dated Oct. 16, 2020.
Notice to File Missing Parts for U.S. Appl. No. 17/179,116 dated Mar. 3, 2021.
Restriction Requirement for U.S. Appl. No. 16/433,773 dated Dec. 7, 2021.
Restriction Requirement for U.S. Appl. No. 16/478,180 dated May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/611,587, filed Jun. 1, 2017.
U.S. Appl. No. 15/612,325, filed Jun. 2, 2017.

(56) References Cited

OTHER PUBLICATIONS

U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/754,736, filed Apr. 11, 2022.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,977, filed Jan. 30, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.

(56) References Cited

OTHER PUBLICATIONS

U.S. Appl. No. 63/181,695, filed Apr. 29, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and U.S. Pat. No. 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and U.S. Pat. No. 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, dated Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and U.S. Pat. No. 10,390,989, May 29, 2020, 193 pages.
Defendant and Counterclaim Plaintiff Sage Products, LLC'S Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.strykercom/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.

(56) References Cited

OTHER PUBLICATIONS

Lee, et al., "Continuous Fabrication of Wide-Tip Microstructures for Bio-Inspired Dry Adhesives via Tip Inking Process", Journal of Chemistry, Jan. 2, 2019, pp. 1-5.
Macaulay, et al., "A Noninvasive Continence Management System: Development and Evaluation of a Novel Toileting Device for Women", The Wound, Ostomy and Continence Nurses Society, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Parness, et al., "A microfabricated wedge-shaped adhesive array displaying gecko-like dynamic adhesion, directionality", J.R. Soc. Interface, 2009, pp. 1223-1232.
Purewick, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
Tsipenyuk, et al., "Use of biomimetic hexagonal surface texture in friction against lubricated skin", Journal of the Royal Society—Interface, 2014, pp. 1-6.
Advisory Action for U.S. Appl. No. 16/452,258 dated Oct. 26, 2022.
Advisory Action for U.S. Appl. No. 16/478,180 dated Sep. 21, 2022.
Final Office Action for U.S. Appl. No. 16/245,726 dated Nov. 25, 2022.
Final Office Action for U.S. Appl. No. 16/369,676 dated Dec. 5, 2022.
Final Office Action for U.S. Appl. No. 16/433,773 dated Oct. 25, 2022.
Final Office Action for U.S. Appl. No. 16/449,039 dated Aug. 1, 2022.
Final Office Action for U.S. Appl. No. 17/662,700 dated Sep. 30, 2022.
International Search Report and Written Opinion from International Application No. PCT/IB2021/057173 dated Nov. 5, 2021.
International Search Report and Written Opinion from International Application No. PCT/US2021/039866 dated Oct. 7, 2021.
International Search Report and Written Opinion from International Application No. PCT/US2022/011421 dated Jun. 13, 2022.
International Search Report and Written Opinion from International Application No. PCT/US2022/014285 dated Sep. 28, 2022.
International Search Report and Written Opinion from International Application No. PCT/US2022/014749 dated Sep. 28, 2022.
International Search Report and Written Opinion from International Application No. PCT/US2022/015026 dated Oct. 31, 2022.
International Search Report and Written Opinion from International Application No. PCT/US2022/015045 dated Sep. 9, 2022.
International Search Report and Written Opinion from International Application No. PCT/US2022/015073 dated Sep. 8, 2022.
International Search Report and Written Opinion from international Application No. PCT/US2022/015418 dated Nov. 11, 2022.
International Search Report and Written Opinion from International Application No. PCT/US2022/015420 dated Nov. 18, 2022.
International Search Report and Written Opinion from International Application No. PCT/US2022/015492 dated Apr. 26, 2022.
International Search Report and Written Opinion from International Application No. PCT/US2022/015781 dated May 6, 2022.
International Search Report and Written Opinion from International Application No. PCT/US2022/018159 dated Dec. 12, 2022.
International Search Report and Written Opinion from International Application No. PCT/US2022/019480 dated Jun. 13, 2022.
International Search Report and Written Opinion from International Application No. PCT/US2022/021103 dated Jun. 23, 2022.
International Search Report and Written Opinion from International Application No. PCT/US2022/022111 dated Oct. 26, 2022.
International Search Report and Written Opinion from International Application No. PCT/US2022/023594 dated Jul. 12, 2022.
International Search Report and Written Opinion from International Application No. PCT/US2022/026667 dated Aug. 22, 2022.
International Search Report and Written Opinion from International Application No. PCT/US2022/030685 dated Oct. 31, 2022.
International Search Report and Written Opinion from International Application No. PCT/US2022/031032 dated Sep. 9, 2022.
International Search Report and Written Opinion from International Application No. PCT/US2022/032424 dated Oct. 11, 2022.
International Search Report and Written Opinion from International Application No. PCT/US2022/034457 dated Oct. 12, 2022.
International Search Report and Written Opinion from International Application No. PCT/US2022/034744 dated Dec. 9, 2022.
International Search Report and Written Opinion from International Application No. PCT/US2022/039714 dated Nov. 22, 2022.
International Search Report and Written Opinion from International Application No. PCT/US2022/042719 dated Dec. 5, 2022.
International Search Report and Written Opinion from International Application No. PCT/US2022/044107 dated Dec. 23, 2022.
Issue Notification for U.S. Appl. No. 16/905,400 dated Nov. 30, 2022.
Non-Final Office Action for U.S. Appl. No. 16/478,180 dated Dec. 20, 2022.
Non-Final Office Action for U.S. Appl. No. 17/051,550 dated Dec. 15, 2022.
Non-Final Office Action for U.S. Appl. No. 17/451,345 dated Dec. 7, 2022.
Non-Final Office Action for U.S. Appl. No. 17/662,700 dated Jul. 22, 2022.
Notice of Allowance for U.S. Appl. No. 16/449,039 dated Dec. 15, 2022.
Notice of Allowance for U.S. Appl. No. 16/899,956 dated Aug. 10, 2022.
Notice of Allowance for U.S. Appl. No. 16/899,956 dated Dec. 1, 2022.
Notice of Allowance for U.S. Appl. No. 16/905,400 dated Aug. 17, 2022.
Notice of Allowance for U.S. Appl. No. 17/461,036 dated Oct. 6, 2022.
U.S. Appl. No. 17/664,914, filed May 25, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 17/999,648, filed Nov. 22, 2022.
U.S. Appl. No. 18/003,029, filed Dec. 22, 2022.
U.S. Appl. No. 62/967,158, filed Jan. 26, 2020.
U.S. Appl. No. 62/991,754, filed Mar. 19, 2020.
U.S. Appl. No. 63/241,328, filed Sep. 7, 2021.
Advisory Action for U.S. Appl. No. 16/245,726 dated Apr. 19, 2023.
Advisory Action for U.S. Appl. No. 16/369,676 dated Mar. 24, 2023.
Advisory Action for U.S. Appl. No. 16/433,773 dated Feb. 15, 2023.
Advisory Action for U.S. Appl. No. 17/662,700 dated Jan. 30, 2023.
Final Office Action for U.S. Appl. No. 17/051,399 dated Mar. 9, 2023.
International Search Report and Written Opinion from International Application No. PCT/US2022/039018 dated Jan. 10, 2023.
International Search Report and Written Opinion from International Application No. PCT/US2022/039022 dated Jan. 10, 2023.
International Search Report and Written Opinion from International Application No. PCT/US2022/039711 dated Jan. 12, 2023.
International Search Report and Written Opinion from International Application No. PCT/US2022/041085 dated Mar. 16, 2023.

(56) References Cited

OTHER PUBLICATIONS

International Search Report and Written Opinion from International Application No. PCT/US2022/042725 dated Dec. 19, 2022.
International Search Report and Written Opinion from International Application No. PCT/US2022/044212 dated Jan. 20, 2023.
International Search Report and Written Opinion from International Application No. PCT/US2022/044243 dated Feb. 24, 2023.
Issue Notification for U.S. Appl. No. 16/899,956 dated Mar. 29, 2023.
Non-Final Office Action for U.S. Appl. No. 16/433,773 dated Apr. 11, 2023.
Non-Final Office Action for U.S. Appl. No. 16/452,145 dated Mar. 28, 2023.
Non-Final Office Action for U.S. Appl. No. 16/452,258 dated Apr. 26, 2023.
Non-Final Office Action for U.S. Appl. No. 16/904,868 dated Mar. 15, 2023.
Non-Final Office Action for U.S. Appl. No. 17/051,585 dated Mar. 29, 2023.
Non-Final Office Action for U.S. Appl. No. 17/179,116 dated Mar. 24, 2023.
Non-Final Office Action for U.S. Appl. No. 17/444,792 dated Feb. 10, 2023.
Non-Final Office Action for U.S. Appl. No. 17/446,256 dated Apr. 13, 2023.
Non-Final Office Action for U.S. Appl. No. 17/448,811 dated Mar. 1, 2023.
Non-Final Office Action for U.S. Appl. No. 17/453,260 dated Mar. 14, 2023.
Non-Final Office Action for U.S. Appl. No. 17/653,137 dated Apr. 7, 2023.
Non-Final Office Action for U.S. Appl. No. 17/655,464 dated Mar. 14, 2023.
Notice of Allowance for U.S. Appl. No. 17/461,036 dated Feb. 22, 2023.
Notice of Allowance for U.S. Appl. No. 17/662,700 dated Mar. 28, 2023.
Restriction Requirement for U.S. Appl. No. 17/326,980 dated Mar. 20, 2023.
Restriction Requirement for U.S. Appl. No. 17/446,256 dated Jan. 23, 2023.
Restriction Requirement for U.S. Appl. No. 17/646,771 dated Apr. 6, 2023.
Text Messages to Lorena Eckert Re Prototype PureWick Holder dated Apr. 16, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/164,800, filed Feb. 6, 2023.
U.S. Appl. No. 18/246,121, filed Mar. 21, 2023.
U.S. Appl. No. 18/247,986, filed Apr. 5, 2023.
U.S. Appl. No. 18/299,788, filed Apr. 13, 2023.
U.S. Appl. No. 63/308,190, filed Feb. 9, 2022.
Final Office Action for U.S. Appl. No. 16/478,180 dated May 31, 2023.
Final Office Action for U.S. Appl. No. 17/051,550 dated May 23, 2023.
Final Office Action for U.S. Appl. No. 17/051,585 dated Jul. 27, 2023.
Final Office Action for U.S. Appl. No. 17/444,792 dated Jun. 15, 2023.
Final Office Action for U.S. Appl. No. 17/448,811 dated Aug. 3, 2023.
Final Office Action for U.S. Appl. No. 17/451,345 dated May 3, 2023.
International Search Report and Written Opinion from International Application No. PCT/US2022/041688 dated Nov. 21, 2022.
International Search Report and Written Opinion from International Application No. PCT/US2022/043818 dated Mar. 24, 2023.
International Search Report and Written Opinion from International Application No. PCT/US2022/044208 dated May 8, 2023.
International Search Report and Written Opinion from International Application No. PCT/US2022/049300 dated Jun. 6, 2023.
Non-Final Office Action for U.S. Appl. No. 16/449,039 dated Apr. 27, 2023.
Non-Final Office Action for U.S. Appl. No. 17/326,980 dated Jul. 11, 2023.
Non-Final Office Action for U.S. Appl. No. 17/450,864 dated May 10, 2023.
Non-Final Office Action for U.S. Appl. No. 17/451,354 dated May 3, 2023.
Non-Final Office Action for U.S. Appl. No. 17/501,591 dated Apr. 25, 2023.
Non-Final Office Action for U.S. Appl. No. 17/646,771 dated Jul. 5, 2023.
Non-Final Office Action for U.S. Appl. No. 17/661,090 dated Jul. 6, 2023.
Non-Final Office Action for U.S. Appl. No. 17/663,330 dated Jun. 29, 2023.
Non-Final Office Action for U.S. Appl. No. 17/664,487 dated Jun. 8, 2023.
Notice of Allowance for U.S. Appl. No. 16/245,726 dated Jul. 6, 2023.
Notice of Allowance for U.S. Appl. No. 17/051,554 dated Jul. 6, 2023.
Notice of Allowance for U.S. Appl. No. 17/461,036 dated Jun. 30, 2023.
Notice of Allowance for U.S. Appl. No. 17/662,700 dated Jul. 28, 2023.
Notice of Allowance for U.S. Appl. No. 18/299,788 dated Jul. 24, 2023.
Restriction Requirement for U.S. Appl. No. 17/657,474 dated Jun. 30, 2023.
U.S. Appl. No. 17/664,487, filed May 23, 2022.
U.S. Appl. No. 18/140,163, filed Apr. 27, 2023.
U.S. Appl. No. 18/140,751, filed Apr. 28, 2023.
U.S. Appl. No. 18/198,464, filed May 17, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/335,579, filed Jun. 15, 2023.
*PureWick Corporation* v. *Sage Products, LLC* Transcripts vol. 5, Apr. 1, 2022, 72 pages.
*PureWick Corporation* v. *Sage Products, LLC* Transcripts vol. 1, Mar. 28, 2022, 99 pages.
*PureWick Corporation* v. *Sage Products, LLC* Transcripts vol. 2, Mar. 29, 2022, 106 pages.
*PureWick Corporation* v. *Sage Products, LLC* Transcripts vol. 3, Mar. 30, 2022, 115 pages.
*PureWick Corporation* v. *Sage Products, LLC* Transcripts vol. 4, Mar. 31, 2022, 117 pages.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.

(56) References Cited

OTHER PUBLICATIONS

"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
Pieper, et al., "An external urine-collection device for women: A clinical trial", Journal of ER Nursing, vol. 20, No. 2, Mar./Apr. 1993, pp. 51-55.
Vinas, "A Solution For An Awkward—But Serious—Subject", http://www.aero-news.net/index.cfm?do=main.textpost&id=69ae2bb1-838b-4098-a7b5-7flbb2505688 last accessed Feb. 8, 2021, 3 pages.

* cited by examiner

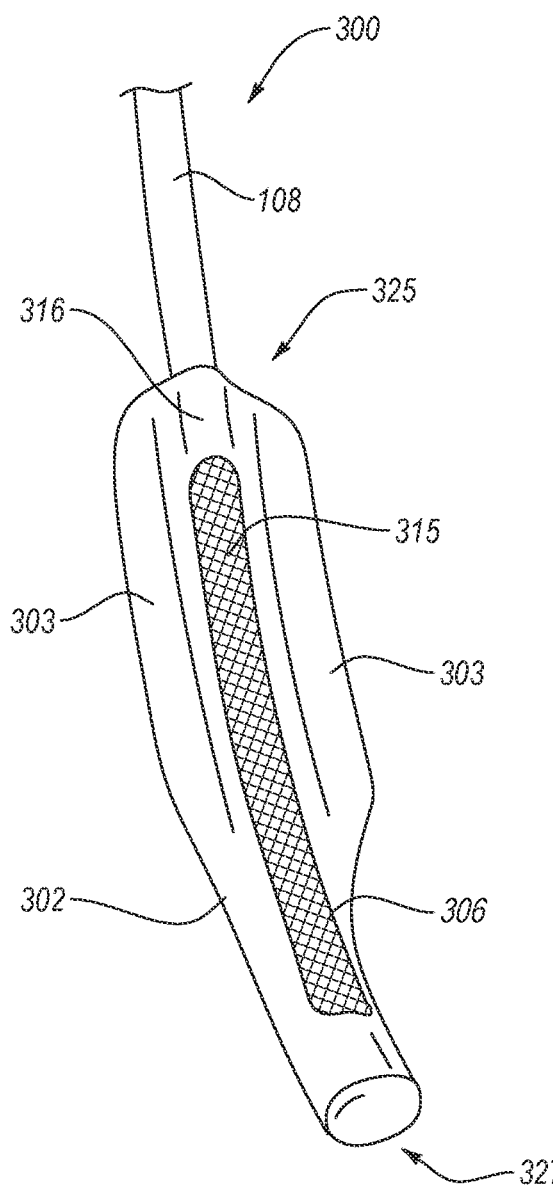
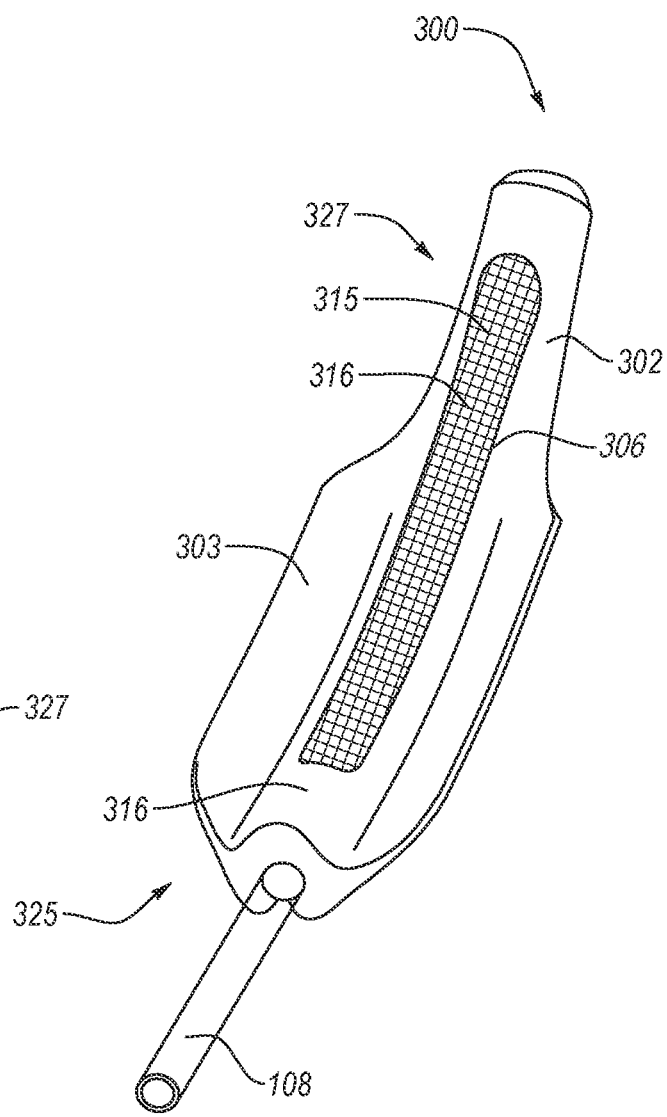
FIG. 8
FIG. 9

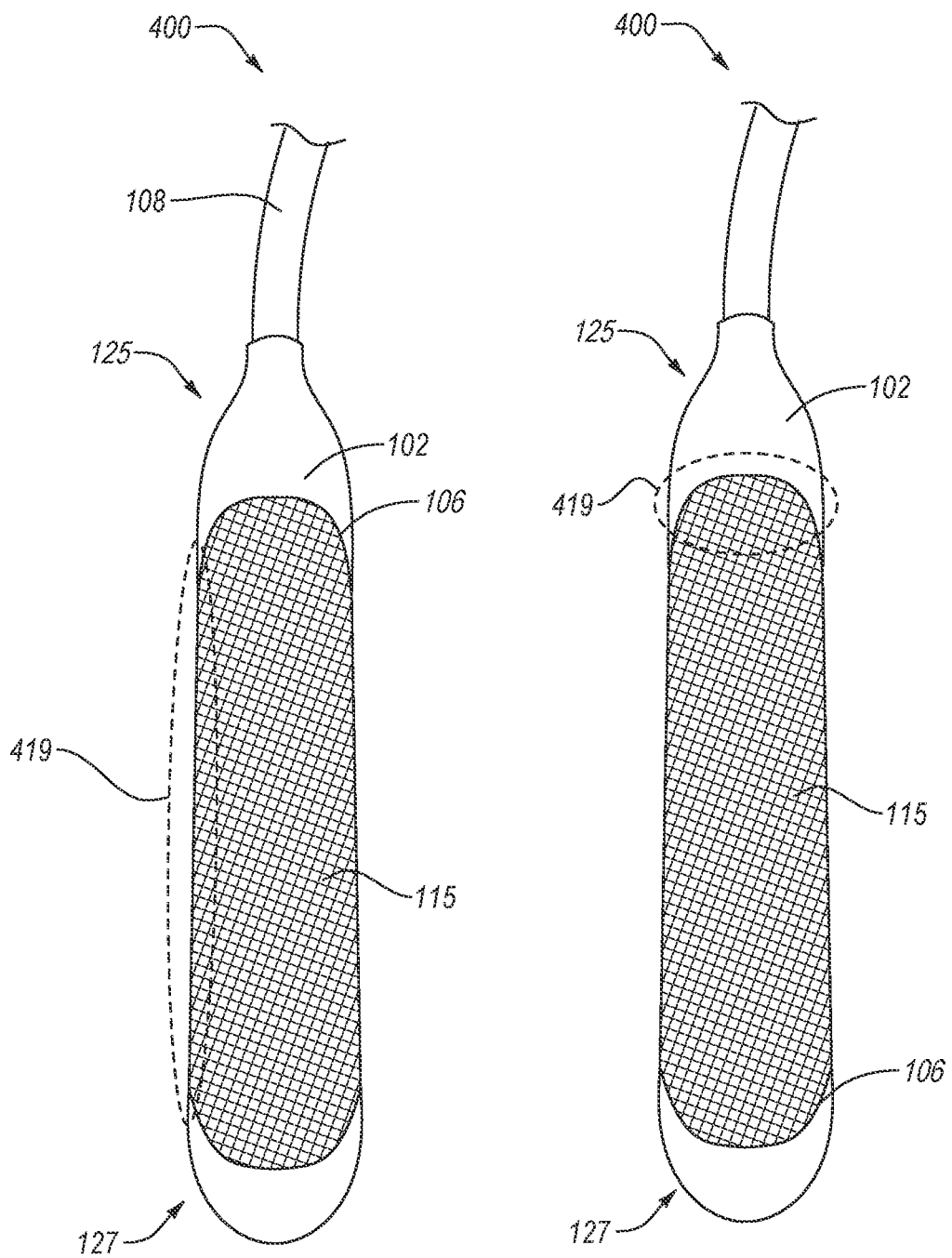

US 11,865,030 B2

VARIABLE FIT FLUID COLLECTION DEVICES, SYSTEMS, AND METHODS

CROSS-REFERENCE TO RELATED APPLICATIONS

This application is a U.S. Nationalization of PCT International Application No. PCT/US2022/012794 filed on Jan. 18, 2022, which claims priority to U.S. Provisional Patent Application No. 63/138,878 filed on 19 Jan. 2021, the disclosure of each of which is incorporated herein, in its entirety, by this references.

BACKGROUND

An individual may have limited or impaired mobility such that utilizing a restroom is challenging or impossible. For example, the individual may have a condition, had a surgery, or a have disability that impairs mobility. Additionally, bodily fluid collection from the individual may be needed for monitoring purposes or clinical testing.

Bedpans and other common urine collection devices suffer from various drawbacks, such as difficulty of use, embarrassing visibility of urine in the device, and some devices cannot be worn at all times, thereby making spills and leakage a risk. Thus, users and manufacturers of patient care beds continue to seek new and improved devices, systems, and methods to prevent patient's clothing and beds from becoming soiled.

SUMMARY

Embodiments disclosed herein are related to fluid collection devices, systems, and methods of collecting fluid from wearers, where the fluid collection devices include a retention means for maintaining the position of the fluid collection device with respect to the wearer In an embodiment, a fluid collection device is disclosed. The fluid collection device includes a fluid impermeable barrier defining an interior chamber therein and an opening through which the interior chamber is accessible. The fluid collection device includes a porous material disposed in the interior chamber. The fluid collection device includes a conduit fluidly connected to the interior chamber. The fluid collection device includes a retention means for retaining positioning of the fluid collection device with respect to the wearer.

In an embodiment, a fluid collection system is disclosed. The fluid collection system includes a fluid storage container configured to hold a fluid. The fluid collection system includes a fluid collection device having a fluid impermeable barrier defining an interior chamber therein and an opening through which the interior chamber is accessible, a porous material disposed in the interior chamber, a conduit fluidly connected to the interior chamber, a retention means for retaining positioning of the fluid collection device with respect to the wearer. The fluid collection system includes at least one vacuum source fluidly coupled to the fluid storage container, the at least one vacuum source configured to draw fluid into the at least one fluid storage container from the fluid collection device via the conduit.

In an embodiment, a method for collecting fluid is disclosed. The method includes positioning a fluid collection device on a wearer, the fluid collection device including a fluid impermeable barrier defining an interior chamber therein and an opening through which the interior chamber is accessible, a porous material disposed in the interior chamber, a conduit fluidly connected to the interior chamber, and a retention means for retaining positioning of the fluid collection device with respect to the wearer. The method includes engaging the retention means of the fluid collection device. The method includes receiving fluid into the fluid collection device.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIGS. 8 and 9 are isometric views of a fluid collection device, according to an embodiment.

FIGS. 11 and 12 are top views of a fluid collection device having a mucoadhesive applied thereto, according to an embodiment.

DETAILED DESCRIPTION

Embodiments disclosed herein are related to devices, systems, and methods for collecting fluid with fluid collection devices having means for retaining position with respect to a wearer. The devices, systems, and methods of disclosed herein include fluid collection devices having a fluid impermeable barrier defining an interior chamber therein, a porous material disposed at least partially within the interior chamber, and a conduit extending into the interior chamber to remove fluids collected within the interior chamber by the porous material. The retention means allow the porous material of the fluid collection device to remain positioned on or over the urethra of the wearer during use. The various retention means provide one or more of conformational rigidity, conformability to wearer anatomy, friction fit with wearer anatomy, or mucoadhesion with wearer anatomy.

Figure 1:
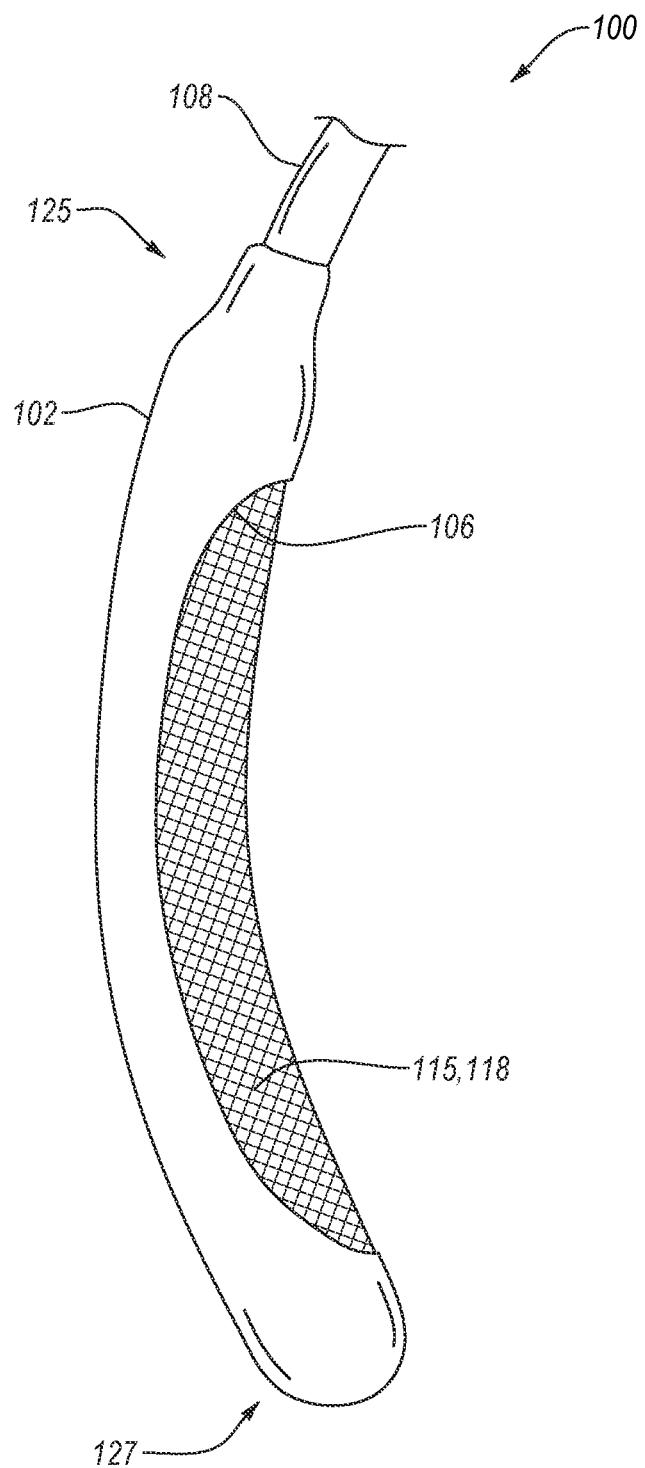
FIG. 1 is a front view of a fluid collection device for females, according to an embodiment.

In a first example, a fluid collection device includes a selectively deformable spine in or around the conduit to maintain a shape of the fluid collection device. FIG. 1 is a front view of a fluid collection device 100 for females, according to an embodiment. The fluid collection device 100 includes a fluid impermeable barrier 102 defining an interior chamber therein and an opening 106. The fluid collection device 100 includes porous material 115 disposed in the interior chamber and exposed through the opening 106. The fluid collection device 100 includes a conduit 108 (e.g., drainage tube) disposed in the interior chamber and entering from the first end region 125 and extending to the second end region 127. The fluid collection device 100 is sized, shaped, and constructed to collect urine or other fluids from the urethra of the wearer.

The fluid impermeable barrier 102 may be formed of any suitable fluid impermeable material(s), such as a fluid impermeable polymer (e.g., silicone, polypropylene, polyethylene, polyethylene terephthalate, thermoplastic elastomer(s), a polycarbonate, etc.), a metal film, natural rubber, another suitable material, or combinations thereof. As such, the fluid impermeable barrier 102 substantially prevents the fluid(s) from passing therethrough. The fluid impermeable barrier 102 at least partially defines the interior chamber (e.g., interior region) therein and the opening 106. For example, the inner surface(s) of the fluid impermeable barrier 102 at least partially defines the interior chamber within the fluid collection device 100. The fluid impermeable barrier 102 at least temporarily retains the fluid(s) in the interior chamber. One or more portions of at least the outer surface of the fluid impermeable barrier 102 may be formed from a soft and/or smooth material, thereby reducing chaffing.

The fluid impermeable barrier 102 may be tubular (ignoring the opening), such as substantially cylindrical (as shown), oblong, prismatic, flattened tube, or any other extruded shape (e.g., a tube having multiple flanges). The fluid impermeable barrier 102 may be sized to fit between the legs of a wearer. During use, the outer surface of the fluid impermeable barrier 102 may at least partially contact the wearer.

The opening 106 provides an ingress route for fluids to enter the interior chamber. The opening 106 may be defined by the fluid impermeable barrier 102, such as by an inner edge of the fluid impermeable barrier 102. For example, the opening 106 is formed in and extends through the fluid impermeable barrier 102, from the outer surface to the inner surface, thereby enabling fluid(s) to enter the interior chamber from outside of the fluid collection device 100. The opening 106 is located and shaped to be positioned adjacent to a wearer's urethra while the device is in use. At least a portion of porous material(s) 115 disposed in the interior may be exposed through the opening 106 to allow fluids to move inwardly into the interior chamber, such as via one or more of permeation, suction, or wicking.

The fluid collection device 100 may be positioned proximate to the urethra and urine may enter the interior chamber via the opening 106. When in use, the opening 106 may be elongated, extending from a first location below the urethra to a second location above the urethra (e.g., at or near the top of the vaginal opening or the pubic region). The opening 106 may exhibit an elongated shape because the space between the legs of a wearer is relatively narrow when the legs of the wearer are closed, thereby only permitting the flow of the fluid(s) along a path that corresponds to the elongated shape of the opening 106 (e.g., longitudinally extending opening). The opening 106 in the fluid impermeable barrier 102 may exhibit a length that is measured along the longitudinal axis of the fluid collection device 100 that may be at least about 10% of the length of the fluid collection device 100, such as about 10% to about 95% of the length of the fluid collection device 100. The opening 106 in the fluid impermeable barrier 102 may exhibit a width that is measured transverse to the longitudinal axis of the fluid collection device 100 and may be at least about 10% of the circumference of the fluid collection device 100, such as about 10% to about 75% of the circumference of the fluid collection device. The opening 406 may be longitudinally oriented (e.g., having a major axis parallel to the longitudinal axis of the device 100.

Figure 2:
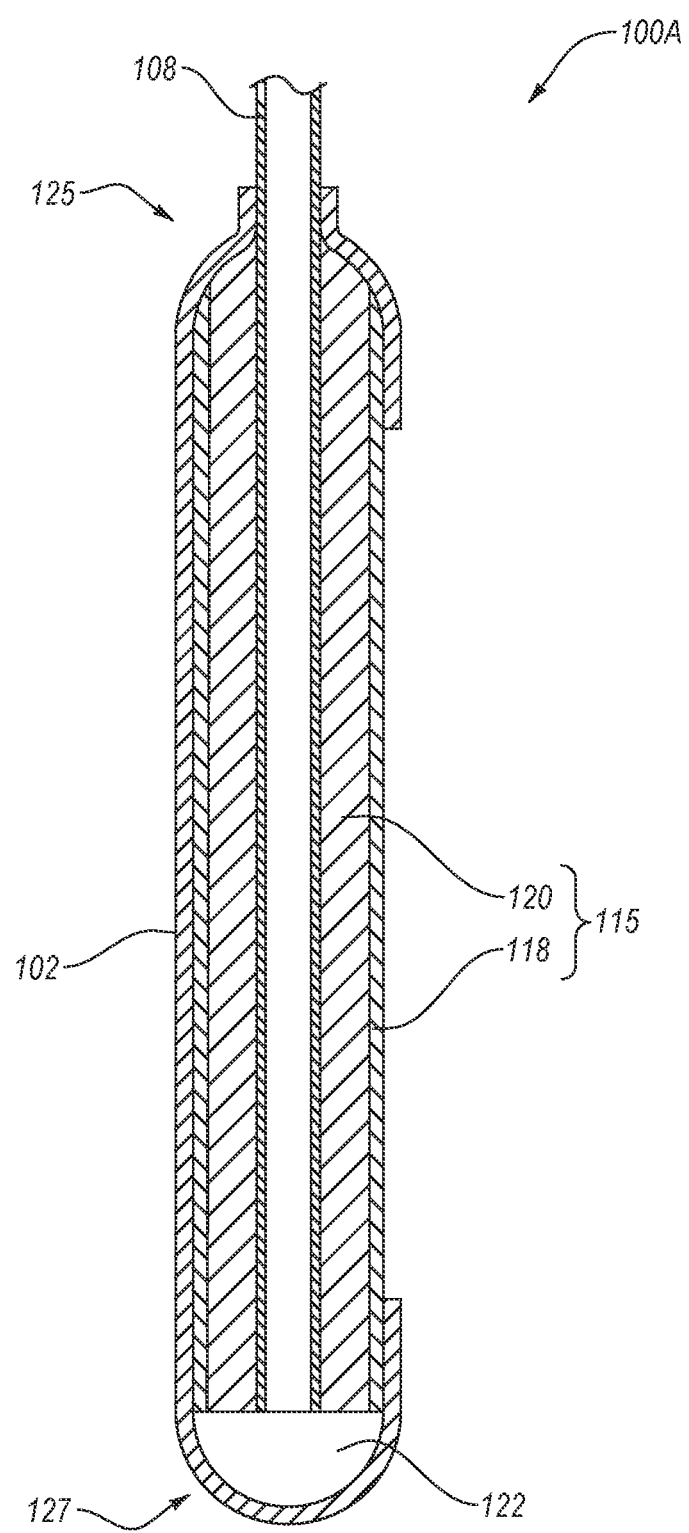
FIG. 2 is a cross-sectional view of the fluid collection device of FIG. 1.

The fluid collection device 100 includes the porous material 115 disposed in the interior chamber. FIG. 2 is a cross-sectional view of the fluid collection device 100. The fluid collection device 100 includes the porous material 115 including a fluid permeable support 120 within a fluid permeable membrane 118 and a conduit 108 extending through the porous material 115. The porous material 115 includes a material that allows fluids to flow therethrough. For example, the porous material 115 may be configured to wick any fluid away from the opening 106, thereby preventing the fluid from escaping the interior chamber. The permeable properties of the porous material referred to herein may be wicking, capillary action, diffusion, or other similar properties or processes, and are referred to herein as "permeable" and/or "wicking." Such "wicking" may not include absorption of fluid into the porous material. Put another way, substantially no absorption of fluid into the porous material may take place after the material is exposed to the fluid and removed from the fluid for a time. While no absorption is desired, the term "substantially no absorption" may allow for nominal amounts of absorption of fluid into the porous material (e.g., absorbency), such as less than about 10 wt % of the dry weight of the porous material, less than about 5 wt %, less than about 3 wt %, less than about 1 wt %, or less than about 0.5 wt % of the dry weight of the porous material 115. The porous material 115 may also wick the fluid generally towards a central region or reservoir of the interior chamber.

The porous material 115 may include more than one material arranged concentrically within the interior chamber, such as gauze disposed over spun plastic fibers (e.g., spun nylon fibers). For example, the porous material 115 may include one or more of a fluid permeable membrane 118 or a fluid permeable support 120 disposed thereunder. The fluid permeable membrane 118 may include any porous material or a material that may wick the fluid. For example, the fluid permeable membrane 118 may include fabric, such as a gauze (e.g., a silk, linen, or cotton gauze), another soft fabric, or another smooth fabric. The fluid permeable membrane 118 may include spun plastic fibers (e.g., spun nylon fibers), such as a spun plastic mat or bed. Forming the fluid permeable membrane 118 from gauze, soft fabric, and/or smooth fabric may reduce chafing caused by the fluid collection device 100 against a wearer.

The fluid collection device 100 may include the fluid permeable membrane 118 disposed in the interior chamber. For example, the fluid permeable membrane 118 may cover at least a portion (e.g., all) of the opening 106.

The porous material 115 of the fluid collection device 100 may include the fluid permeable support 120 disposed in the interior chamber below the fluid permeable membrane 118. The fluid permeable support 120 may be composed to support the fluid permeable membrane 118 since the fluid permeable membrane 118 may be formed from a foldable, flimsy, or otherwise easily deformable material. For example, the fluid permeable support 120 may be positioned such that the fluid permeable membrane 118 is disposed between the fluid permeable support 120 and the fluid impermeable barrier 102. As such, the fluid permeable support 120 may support and maintain the position of the fluid permeable membrane 118 thereon. The fluid permeable support 120 may include any porous, fluid permeable material, such as a material that may wick the fluid. For example, the fluid permeable support 120 may include any of the fluid permeable membrane materials disclosed herein. The fluid permeable support 120 may be formed from any fluid porous material that is less deformable than the fluid permeable membrane 118, such as any of the materials disclosed herein for the fluid permeable membrane 118, in a more dense or rigid form. In some examples, the fluid permeable support 120 may include a porous polymer (e.g., nylon, polyester, polyurethane, polyethylene, polypropylene, etc.) structure, an open cell foam, or spun plastic fibers (e.g., nylon fibers). In some examples, the fluid permeable membrane 118 may include gauze and the fluid permeable support 120 may include spun nylon fibers. In some examples, the fluid permeable support 120 may be formed from fabric, felt, gauze, or combinations thereof. In some examples, the fluid permeable support 120 may be formed from a natural material, such as cotton, wool, silk, or combinations thereof. In such examples, the material may have a coating to prevent or limit absorption of fluid into the material, such as a water repellent coating. In some examples, the fluid permeable support 120 may be omitted from the fluid collection device 100. In some examples, the fluid permeable membrane 118 may be optional. For example, the porous material 115 may include only the fluid permeable support 120.

The fluid permeable support may have a greater permeability or a greater ability to wick fluids than the fluid permeable membrane 118, such as to move the fluid inwardly from the outer surface of the fluid collection device 100 through the permeable membrane 118 and into the fluid permeable support. In some examples, the permeability or the wicking ability of the fluid permeable support and the fluid permeable membrane 118 may be substantially the same.

The fluid impermeable barrier 102, the porous material 115 may be sized and shaped to have the conduit 108 at least partially disposed in the interior chamber. For example, at least one of the fluid permeable membrane 118 and the fluid permeable support 120 may be configured to form a space that accommodates the conduit 108. The fluid impermeable barrier 102 may define an aperture sized to receive the conduit 108 therethrough. The aperture may be sized and shaped to form an at least substantially fluid tight seal against the conduit 108 thereby substantially preventing the fluid(s) from escaping the interior chamber. The fluid collected in the fluid collection device 100 may be removed from the interior chamber via the conduit 108.

The porous material 115 may extend across at least a portion (e.g., all) of the opening 106. At least a portion of the porous material 115 may be exposed to an environment outside of the interior chamber through the opening 106. The fluid permeable membrane 118 and the fluid permeable support 120 may at least substantially completely fill the portions of the interior chamber that are not occupied by the conduit 108. In another example, the fluid permeable membrane 118 and the fluid permeable support 120 may not substantially completely fill the portions of the interior chamber that are not occupied by the conduit 108. In such an example, the fluid collection device 100 includes reservoir 122 in the interior chamber. The reservoir 122 is defined between the fluid impermeable barrier 102 and the porous material 115 in the interior chamber. The reservoir 122 may be located in a portion of the fluid collection device 100 expected to be positioned in a gravimetrically low point of thereof when worn by a user. While depicted in the second end region 127, the reservoir 122 may be located in any portion of the interior chamber such as the first end region 125.

As shown in FIG. 1, the fluid collection device 100 includes conduit 108 (e.g., drainage tube) which extends in the interior chamber. The conduit 108 may include a flexible material such as polymer tubing (e.g., medical tubing) material. Such polymer tubing material may include a thermoplastic elastomer, polyvinyl chloride, ethylene vinyl acetate, polytetrafluoroethylene, etc., tubing. In some examples, the conduit 108 may include silicon or latex. In some examples, the conduit 108 may include one or more portions that are resilient, such as to by having one or more of a diameter or wall thickness that allows the conduit 108 to be flexible. In some examples, the conduit 108 may be frosted or opaque (e.g., black) to obscure visibility of the fluid(s) therein.

The conduit 108 includes an inlet at a first end region and an outlet at a second end region positioned downstream from the inlet. The conduit 108 may extend into the interior chamber to any point therein. For example, the conduit 108 may be inserted into the interior chamber at the first end region 125 of the fluid collection device 100 and extend therethrough to the second end region 127. The conduit 108 may extend into the fluid impermeable barrier 102 from the first end region 125 through to the second end region 127 to a point proximate to the reservoir 122 such that the inlet is in fluid communication with the reservoir 122. In some examples (not shown), the conduit 108 may enter the interior chamber in the second end region 127 and the inlet of the conduit 108 may be disposed in the second end region 127 (e.g., in the reservoir 122 or flush with fluid impermeable barrier 102). The fluid collected in the reservoir 122 may be removed from the interior chamber via the conduit 108. In some examples, the inlet may be disposed at the end of the porous material 115 in the second end region 127, such as flush with the end of the fluid permeable support 120. In some examples, the inlet of the conduit 108 may be disposed within the fluid permeable support 120 such between first end region 125 and the second end region 127.

Other examples of fluid impermeable barriers, porous materials, chambers, conduits and their shapes and configurations are disclosed in U.S. patent application Ser. No. 15/612,325 filed on Jun. 2, 2017; U.S. patent application Ser. No. 15/260,103 filed on Sep. 8, 2016; and U.S. Pat. No. 10,226,376 filed on Jun. 1, 2017, the disclosure of each of which is incorporated herein, in its entirety, by this reference.

The conduit 108 provides a selectively deformable spine within the fluid collection device 100. Upon manual manipulation, the conduit 108 may hold the fluid collection device 100 in a specific shape, such as the illustrated curved shape. For example, the fluid collection device 100 is able to deform to the curvature of the body between the glutes and the labia by manipulating the conduit 108. The reduction in tension along the spine of the fluid collection device 100 provided by the conduit 108 reduces the likelihood of detachment or misalignment of the fluid collection device 100 from the urethra (e.g., on top of the labia).

Figure 3:
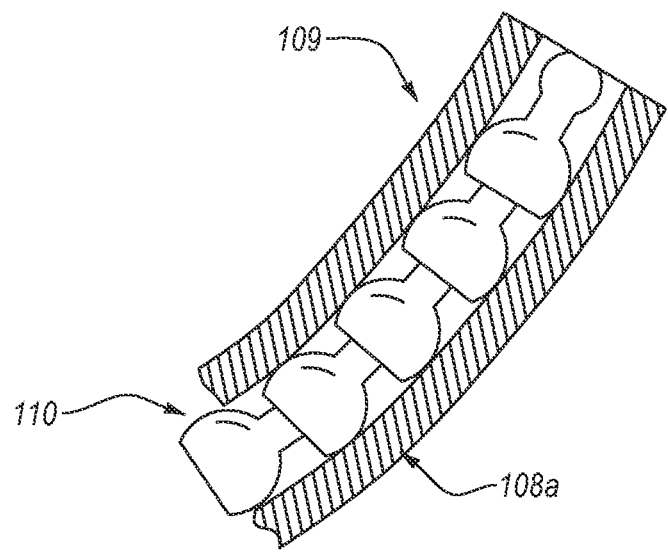
FIGS. 3 and 4 are cross-sectional views of a deformable conduit, according to an embodiment.
Figure 4:
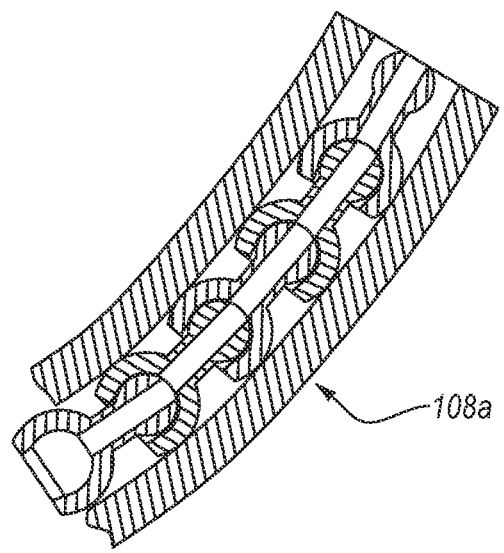

Disclosed below are examples for the conduit 108 to provide a selectively deformable spine in the fluid collection device 100. FIGS. 3 and 4 are cross-sectional views of a deformable conduit 108a, according to an embodiment. As shown in FIG. 3, the deformable conduit 108a includes tubing 109 disposed over flexible gooseneck tubing 110. The gooseneck tubing 110 may be a modular hose that is capable of manipulation responsive to external forces and rigid retention of a selected configuration after manipulation. For example, the gooseneck tubing 110 may include a ball and socket construction such as a Loc-Line® type modular hose or the like. The size of the balls and sockets of the gooseneck tubing 110 provide a selected fit therebetween (e.g., slip fit, interference fit, etc.) to provide a selected amount of resistance to deformation. Accordingly, the deformable conduit 108a may be selectively shaped (e.g., deformed) and retain the selected shape or conformation. In some examples, the gooseneck tubing 110 may be constructed of polymer balls and sockets.

As shown in FIG. 4, the gooseneck tubing 110 includes an interior passageway therein for enabling fluid to move therethrough. The interior passageway is formed by the interior walls of the balls and sockets of the gooseneck tubing, which have a selected bore size therein. The fluids (e.g., urine) collected in the fluid collection device having the deformable conduit 108a flow though the interior passageway of the deformable conduit 108a as the fluid drains therefrom.

The gooseneck tubing 110 may or may not be fluid tight. Accordingly, the tubing 109 therearound may help retain fluids within the deformable conduit 108a. The tubing 109 may be relatively soft and flexible compared to conventional drainage tubing. The tubing 109 provides a cushion between the wearer and the gooseneck tubing 110. The tubing 109 may be constructed of a polymer such as a thermoplastic elastomer, polyvinyl chloride, ethylene vinyl acetate, polytetrafluoroethylene, etc., or combinations of any of the foregoing. In some examples, the tubing 109 may include silicone or latex. The tubing 109 may have a wall thickness of at least about 1 mm, such as about 1 mm to about 5 mm, or less than 10 mm. The deformable conduit 108a may include tubing 109 having a thickness that prevents wearers from feeling the gooseneck tubing 110 therebelow.

The diameter or greatest dimension of the gooseneck tubing 110 may be about 13 mm or less, such as about 5 mm to about 13 mm, about 5 mm to about 8 mm, about 8 mm to about 13 mm, or more than about 8 mm. In some examples, the diameter or greatest dimension of the deformable conduit 108a (including the outer dimensions of the tubing 109 disposed over the gooseneck tubing 110) may be about 13 mm or less, such as about 5 mm to about 13 mm, about 5 mm to about 8 mm, about 8 mm to about 13 mm, or more than about 8 mm. Fluid collection devices incorporating the deformable conduit 108a may include porous material having a thickness that prevents wearers from feeling the gooseneck tubing 110 of the deformable conduit 108a therebelow.

The gooseneck tubing 110 may extend only along a portion of the deformable conduit 108a, such as the portion inside of the interior chamber or from inside of the interior chamber to a distance outside of the first end region 125 of the fluid collection device containing the same, such as at least 1 cm past the aperture through which the conduit 108a is inserted into the fluid collection device. The deformable conduit 108a may be used in any of the examples of fluid collection devices disclosed herein.

Figure 5:
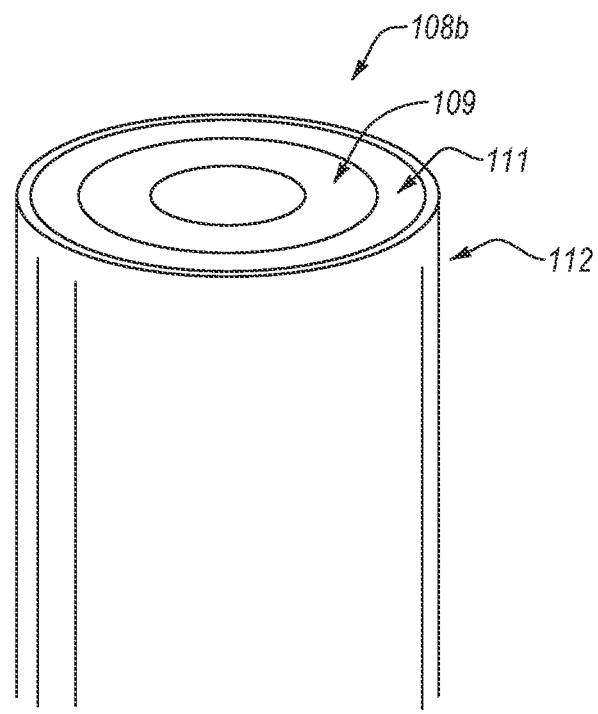
FIG. 5 is an isometric view of a portion of a deformable conduit, according to an embodiment.
Figure 6:
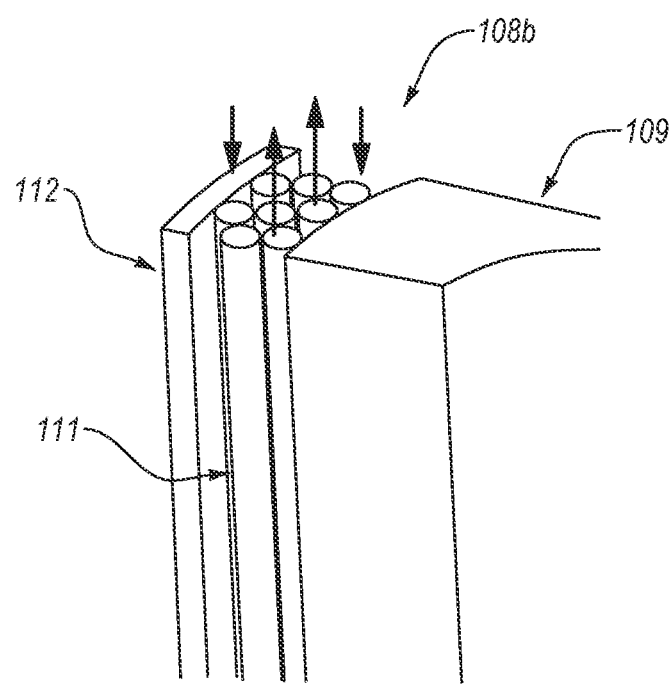
FIG. 6 is a close-up partial cut-away view of the deformable conduit of FIG. 5.

Different deformable conduits may be utilized in fluid collection devices. FIG. 5 is an isometric view of a portion of the deformable conduit 108b, according to an embodiment. FIG. 6 is a close-up partial cut-away view of the deformable conduit 108b of FIG. 5. The deformable conduit 108b may include a plurality of fibers 111 sandwiched between tubing 109 and an outer tube 112. The plurality of fibers 111 may include polymer fibers or wires. The plurality of fibers may include wires including one or more of polycarbonate, polyethylene, polyvinylchloride, polypropylene, polyolefin, fluorinated polymers (polytetrafluoroethylene), polyamide, or the like. The width of the fibers or wires may be 0.1 mm or more, such as 0.1 mm to 3 mm, 0.1 mm to 1 mm, 1 mm to 3 mm, less than 3 mm, or less than 1 mm. As the deformable conduit 108b is bent, the polymer fibers move past each other and the friction therebetween holds them in the new position to prevent spring back. The plurality of fibers may be packed between the outer tube 112 and the tubing 109 with a selected spacing to provide a selected fit therebetween, such as a slip fit, a tension fit, an interference fit, or the like. The tightness of the packing within the plurality of fibers 111 can provide fine tuning of the stiffness of the deformable conduit 108b. Accordingly, the deformable conduit 108b may retain a selected shape according to manual manipulation and may resist forces of a selected magnitude to change the shape.

The tubing 109 may be as disclosed herein with respect to the deformable conduit 108a. The outer tube 112 may be similar or identical to the conduit 108 or the tubing 109, in one or more aspects. For example, the outer tubing 112 may including a polymer conduit, such as thermoplastic elastomer, polyvinyl chloride, ethylene vinyl acetate, polytetrafluoroethylene, silicone, latex, or combinations thereof.

The plurality of fibers 111, tubing 109, and outer tube may extend only along a portion of the deformable conduit 108b, such as the portion inside of the interior chamber or from inside of the interior chamber to a distance outside of the first end region of the fluid collection device containing the same, such as at least 1 cm past the aperture through which the conduit 108b is inserted into the fluid collection device. The deformable conduit 108b may be used in any of the examples of fluid collection devices disclosed herein.

The deformable conduits 108a and 108b may be sized and shaped to conform the fluid collection devices carrying the same to the anatomy of a wearer along the sagittal plane of the wearer, such as in the pelvic region. Such examples provide fluid collection devices that can be manipulated to a selected shape and may resist changing from the selected shape, such as from movement of the wearer.

Figure 7:
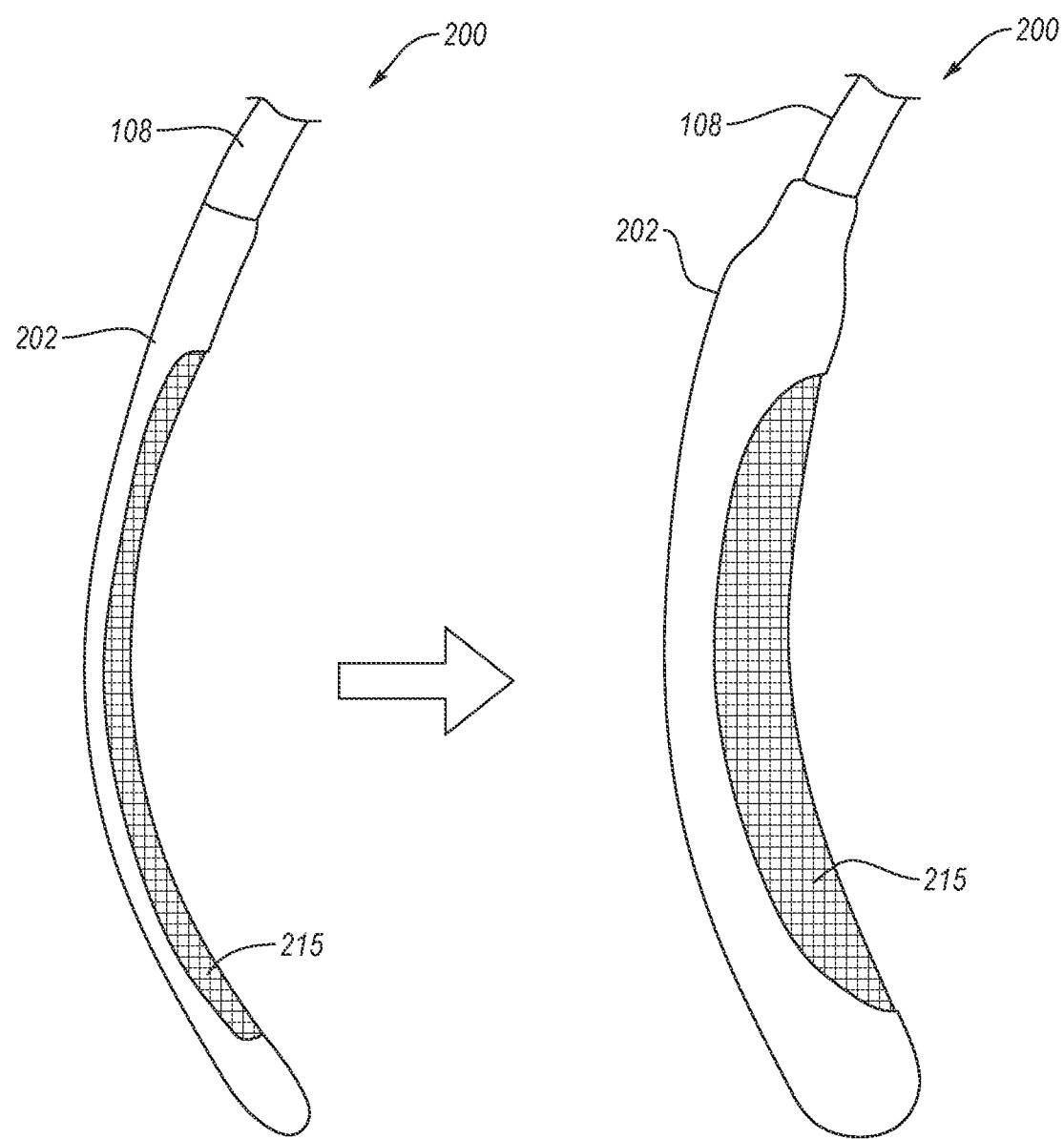
FIG. 7 is a side view of a fluid collection device changing from a compressed to an uncompressed state, according to an embodiment.

In some examples, the fluid collection device may be at least partially held in place by a resiliently compressible design. FIG. 7 is a side view of fluid collection device 200 changing from a compressed to an uncompressed state. The fluid collection device 200 includes the fluid impermeable barrier 202, the porous material 215, and the conduit 108 extending therethrough. The fluid collection device 200 is resiliently compressible and may at least partially hold a shape responsive to pressure applied thereto.

The porous material 215 includes a soft, resilient foam, such as a viscoelastic foam (e.g., memory foam or low-resilience polyurethane). Accordingly, the porous material 215 is compressible. The resilient foam of the porous material 215 is an open cell foam to allow fluids to pass therethrough. The porous material 215 may include one or more of the fluid permeable membrane or the fluid permeable support. The resilient foam of the porous material 215 may be used alone as a fluid permeable membrane or the fluid permeable support. In the latter case, a fluid permeable membrane, such as any of those disclosed herein (e.g., gauze) may be disposed over the resilient foam.

The fluid impermeable barrier 202 is a soft malleable material capable of being deformed and springing back to an original shape, either alone or as forced by the resilient foam of the porous material 215. The fluid impermeable barrier 202 may be similar or identical to the fluid impermeable barrier 102 in one or more aspects. The fluid impermeable barrier 202 may include silicone, rubber, or a polymer as disclosed herein. The fluid impermeable barrier 202 may be thin layer directly attached to the porous material 215, such as a coating thereon. For example, the fluid impermeable barrier may be a waterproof polyurethane laminate fabric or the like, which may be welded directly to the foam or wrapped therearound.

The conduit 108 may be made of a relatively malleable (compared to conventional medical drainage tubing), fluid-tight material. For example, the conduit 108 may be made of one or more of polyethylene, polyvinyl chloride, latex, silicone, or a mixture thereof. Higher amounts of silicone provide a softer, more malleable conduit 108. The conduit 108 is malleable responsive to pressure such that the fluid collection device 200 is not shaped by the stiffness of the conduit 108.

In use, the fluid collection device 200 is compressed and inserted or pressed against the anatomy of the wearer. As the fluid collection device 200 returns to an expanded shape, the fluid collection device 200 at least partially conforms to the anatomy of the wearer. Accordingly, the fluid collection device 200 provides an improved anatomical fit to increase comfort, maintain position on the wearer, and decrease leakage over less conformable materials and devices. The resiliently compressible components (e.g., the resilient foam of the porous material 215) provides a means of retaining the fluid collection device 200 in position on the wearer. The deformable conduits 108a and 108b may be used with the fluid collection device 200.

Figure 10A:
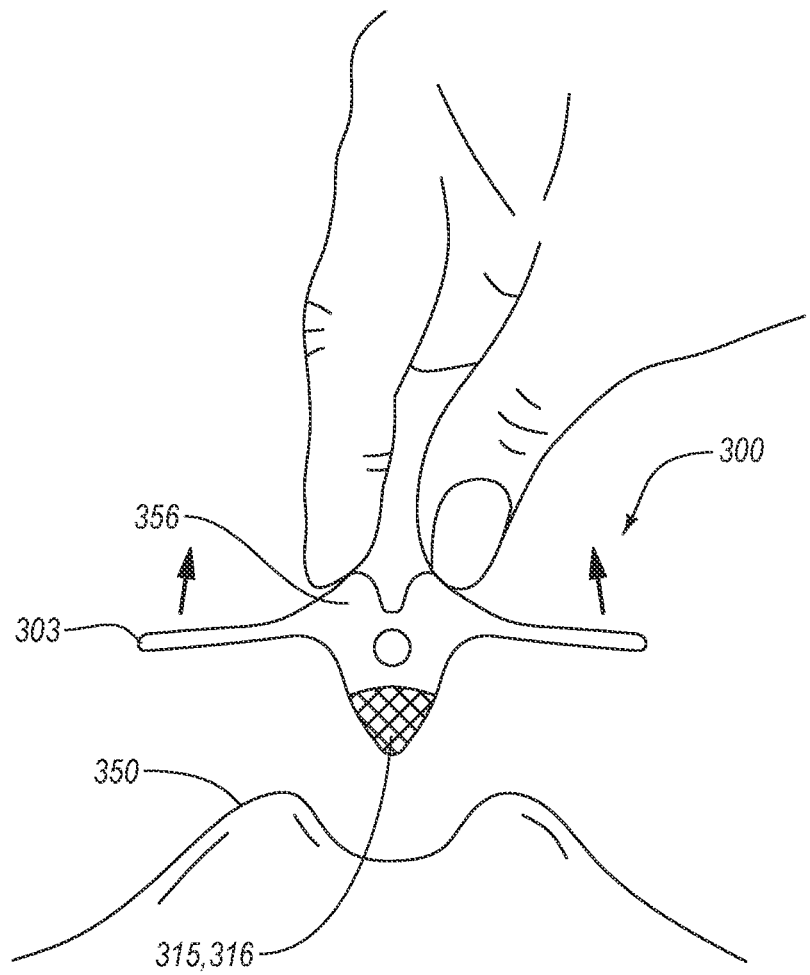
FIGS. 10A and 10B are illustrations of the fluid collection device of FIGS. 8 and 9 in cross-section during positioning.
Figure 10B:
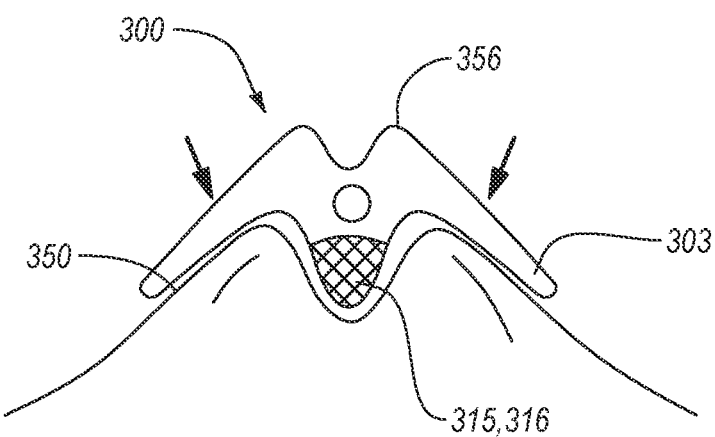

In some examples, the shape of the fluid collection device is generally preformed to the shape of labia and can be manipulated from a closed state to an open state by compression of a portion thereof. FIGS. 8 and 9 are isometric views of fluid collection device 300, according to an embodiment. FIGS. 10A and 10B are illustrations of the fluid collection device 300 in cross-section during positioning. The fluid collection device 300 includes fluid impermeable barrier 302 having labial flanges 303 extending outwardly from a longitudinal axis thereof, porous material 315, the conduit 108, and lobes 356 extending longitudinally along the back of the fluid collection device 300.

The fluid impermeable barrier 302 includes an outer surface and an inner surface that defines an interior chamber therein. The fluid impermeable barrier 302 includes an opening 306. The fluid impermeable barrier 302 at least partially defines the labial flanges 303 and the lobes 356. The porous material 315 is at least partially disposed in the interior chamber and protrudes therefrom through the opening 306. The conduit 108 extends into the interior chamber via fluid impermeable barrier, such as into the porous material (e.g., to a reservoir in the interior chamber). The porous material 315 may be similar or identical to any of the porous material(s) disclosed herein, such as having a fluid permeable membrane and a fluid permeable support. The fluid impermeable barrier 302 is formed of a fluid impermeable material such as any of the fluid impermeable materials disclosed herein.

The labial flanges 303 are shaped with longitudinally extending valleys sized to at least partially accommodate labia majora therein. The labial flanges 303 may be at least partially rigid. The fluid impermeable barrier 302 converges to an apex 316 along the longitudinal axis in the first end region 325. The porous material 315 also includes an apex 316 along the longitudinal axis. Accordingly, the apex 316 may be positioned between the labia majora and the valleys accommodate the labia majora during use. The outer surfaces of the labial flanges 303 (e.g., on the wearer facing surface) may be textured or tacky for frictional engagement with the labia of the wearer. The longitudinal shape of the fluid collection device or portions thereof may be at least slightly arcuate to complement the shape of wearer anatomy.

On the back of the fluid collection device 300, the fluid impermeable barrier 302 defines the lobes 356. The lobes 356 have a valley therebetween. The lobes may longitudinally extend along at least a portion of the back side of the fluid collection device 300. The lobes 356 may be pinched inwardly, as shown in FIGS. 10A and 10B, to open the labial flanges 303 and expose the apex 316. For example, the lateral ends of the labial flanges 303 rotate away from the apex 316 when the lobes 356 are pinched due to tension applied across the fluid impermeable barrier 302. The apex 316 may be inserted between the labia majora 350. Upon release, the lateral ends of the labial flanges 303 rotate back toward the apex 316 to engage the outer surface of the labia majora 350 with the valleys formed between the labial flanges 303 and the apex 316 at least partially containing the labia majora therein. Accordingly, the apex 316 of the porous material 315 may be positioned closer to the urethra of the wearer than cylindrical devices. The labial flanges 303 may hold onto the labia majora, by inward pressure or pinching after the inward pressure on the lobes 356 is released. Accordingly, an additional means of retention is provided by the shape of the fluid collection device 300.

In some examples, a fluid collection device may use a mucoadhesive to increase engagement with the wearer. FIGS. 11 and 12 are top views of a fluid collection device 400 having a mucoadhesive applied thereto, according to an embodiment. The fluid collection device 400 includes the fluid impermeable barrier 102 defining the outer surface and the inner surface which defines the interior chamber of the fluid collection device 400. The fluid collection device 400 includes the porous material 115. The porous material 115 is exposed through the opening 106 in the fluid impermeable barrier 102. The fluid collection device 400 includes the conduit 108 extending into the fluid impermeable barrier 102 and porous material 115 from the first end region to the second end region of the fluid collection device 400. The fluid collection device includes a mucoadhesive applied to at least a portion of the fluid impermeable barrier 102 in the regions 419.

The mucoadhesive in the region 419 adds a tackifier to the fluid impermeable barrier 102 which provides shear resistance with a nearly no impact on peel strength. The mucoadhesive may include a gum, a gel, a polymer, a tape, or combinations thereof. For example, the mucoadhesive gum may include a Tmarind/Xanthum gum or the like. The mucoadhesive in gel form may include a Gantrez/Sodium alginate gel or the like. In some examples, the mucoadhesive includes a tape having surface modifiers thereon, a low tack adhesive with a tackifying additive integrated to the fluid impermeable barrier. Other gums, gels, or polymers may be used. The mucoadhesive may be disposed on one or more portions of the fluid collection device 400, such as on the fluid impermeable barrier 102 in region 419 as shown in FIG. 11 or on the porous material 115 near the top of the opening in region 419 as shown in FIG. 12.

As shown in FIG. 11, the region 419 may be along the sides of the opening through which the porous material 115 is exposed. In such examples, the mucoadhesive may provide increased engagement with the inner legs (thighs) or labia of the wearer.

As shown in FIG. 12, the region 419 may be at the top of the opening through which the porous material 115 is exposed. In such examples, the mucoadhesive may be disposed on the fluid impermeable barrier 102 and/or porous material 115 at the top of the opening in region 419. In such examples, the mucoadhesive provides increased engagement with the pubic region of the wearer, thereby keeping the opening (and porous material 115 therein) over the urethra of the wearer.

The mucoadhesive included on the fluid collection device 400 provides and additional retention means to maintain the positioning of the fluid collection device 400 with respect to the wearer. By limiting the area that the mucoadhesive is disposed on, the wearer, the wearer's clothing, and bedding may be prevented from contamination by the mucoadhesive. Accordingly, the mucoadhesive retains the position of the fluid collection device on the wearer without introducing large amounts of adhesive onto the wearer.

During use, the fluid collection device(s) disclosed herein may be positioned such that the opening of the fluid collection device through which the porous material is exposed is disposed on or over the urethra of the wearer. The fluid collection device may receive bodily fluids (e.g., urine) from the urethra into the internal chamber. At least some of the bodily fluids may be removed from the urethra via the porous material (e.g., via wicking, absorptions, adsorption, etc.). The bodily fluids may flow towards the open end of the conduit in the reservoir (e.g., in the gravimetrically low point of the device) through the porous material in the interior chamber. The bodily fluids may be removed from the fluid collection device via the conduit. Suction force may be introduced into the interior chamber via the conduit responsive to suction (e.g., vacuum) force applied to the conduit by a vacuum source. The bodily fluids removed from the fluid collection device may be stored in the fluid storage container operably coupled to the vacuum source.

Figure 13:
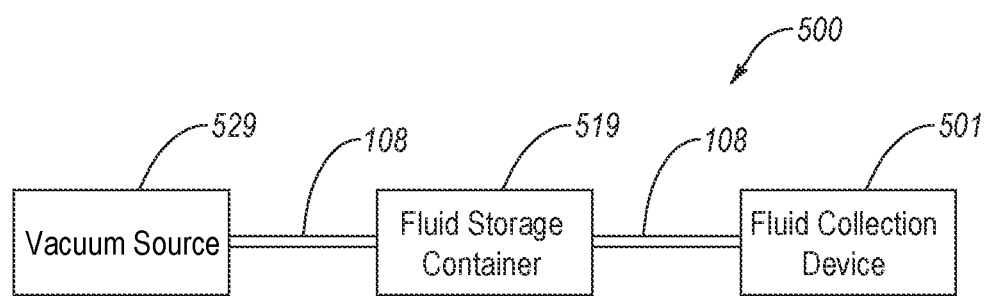
FIG. 13 is a block diagram of a system for collecting fluid, according to an embodiment.

The fluid collection devices disclosed herein may be part of a fluid collection system. FIG. 13 is a block diagram of a system 500 for collecting fluid, according to an embodiment. The system 500 includes a fluid collection device 501 operably coupled to one or more of a fluid storage container 519 or a vacuum source 529, such as via the conduit(s) 108. The conduit 108 may fluidly connect an interior chamber of the fluid collection device 501 with the fluid storage container 519 or the vacuum source 529 (via the fluid storage container 519). Accordingly, fluids may be removed from the interior chamber via the conduit 108 via one or more of gravity feed or vacuum suction.

The fluid collection device 501 may be similar or identical to any of the fluid collection devices disclosed herein. For example, the fluid collection device 501 may include a fluid impermeable barrier, a fluid permeable body, and any of the retention means disclosed herein. The fluid collection device 501 may include the conduit 108 including an inlet and an outlet as disclosed herein. The outlet may be fluidly coupled to the fluid storage container 519 and the inlet may be positioned in the fluid collection device 501.

The conduit 108 is coupled to and at least partially extends between one or more of the fluid storage container 519 and the vacuum source 529. Accordingly, the vacuum source 529 may be fluidly connected to the fluid storage container 519 via the conduit 108. In an example, the conduit 108 is directly connected to the vacuum source 529. In some examples, the conduit 108 may be indirectly connected to at least one of the fluid storage container 519 and the vacuum source 529. In some examples, the conduit 108 may be secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

Fluid (e.g., urine or other bodily fluids) collected in the fluid collection device 501 may be removed from the fluid collection device 501 via the conduit(s) 108. Vacuum or suction force may be applied to remove fluid from the fluid collection device via the conduit either directly or indirectly. The vacuum force may be applied indirectly via the fluid storage container 519. For example, the second open end of the conduit 108 may be disposed within the fluid storage container 519 and an additional conduit 108 may extend from the fluid storage container 519 to the vacuum source 529. Accordingly, the vacuum source 529 may indirectly apply vacuum or suction force into the fluid collection device 501 (e.g., chamber therein) via the fluid storage container 519 and conduit(s) 108. As the fluid is drained from the interior chamber of the fluid collection device 501, the fluid may travel through the first section of conduit 108 to the fluid storage container 519 where it may be retained.

The fluid storage container 519 is constructed to store fluids therein. The fluid storage container may include a bag (e.g., drainage bag), a rigid bottle or cup (e.g., collection jar), or any other enclosed container for storing bodily fluids. The fluid storage container(s) may be fluidly connected to the vacuum source(s) 529, such as via a portion of conduit 108. The vacuum source(s) 529 provides a vacuum for pulling fluids from one or more of the fluid collection device 501 into the fluid storage container 519 via the conduit 108. The fluid collected in the fluid collection device 501 is moved through the conduit into the fluid storage container. By having a separate connection to the vacuum source 529 on the fluid storage container 519, the fluids removed from the fluid collection device 501 may be prevented from entering the vacuum source 529.

The vacuum source may include one or more of a manual vacuum pump, an electric vacuum pump, a diaphragm pump, a centrifugal pump, a displacement pump, a magnetically driven pump, a peristaltic pump, or any pump configured to produce a vacuum. The vacuum source may include a wall mounted suction line, such as found in a hospital room. In examples, the vacuum source may be powered by one or more of a power cord (e.g., connected to a power socket), one or more batteries, or even manual power (e.g., a hand operated vacuum pump). The vacuum source may include one or more of a switch, a button, a plug, a remote, or any other actuator suitable to activate the vacuum source. The vacuum source may be selectively operated by a user (e.g., medical personnel, the wearer, or a caretaker).

Figure 14:
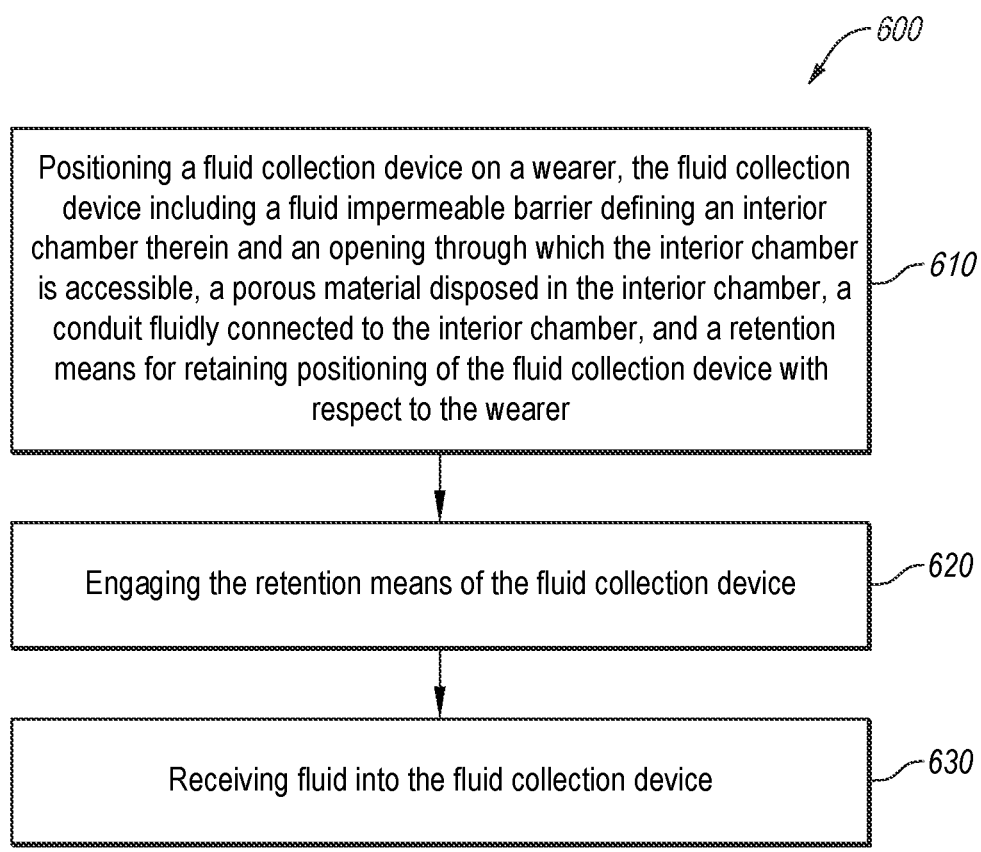
FIG. 14 is a flow diagram of a method for collecting fluid, according to an embodiment.

Any of the fluid collection devices and systems disclosed herein may be utilized to collect fluid, such as urine, from a wearer of the fluid collection device. FIG. 14 is a flow diagram of a method 600 for collecting fluid, according to an embodiment. The method 600 includes the act 610 of positioning a fluid collection devices on a wearer, the fluid collection device including a fluid impermeable barrier defining an interior chamber therein and an opening through which the interior chamber is accessible; a porous material disposed in the interior chamber; a conduit fluidly connected to the interior chamber; and a retention means for retaining positioning of the fluid collection device with respect to the wearer. The method 600 includes the act 620 of engaging the retention means. The method 600 includes the act 630 of receiving fluid in the fluid collection device. Any the acts 610, 620, or 630 of the method 600 may be performed in different orders, split into multiple acts, modified, supplemented, or combined. For example, the acts 610 and 620 may be combined into a single act. In some examples, one or more of the blocks 610-630 of the method 600 may be omitted or additional acts may be added.

Any of the fluid collection devices disclosed herein may be used in the method 600. For example, the act 610 may include positioning any of the fluid collection devices disclosed herein on a wearer in a position to collect urine therefrom. The fluid collection device includes a fluid impermeable barrier defining an interior chamber therein and an opening through which the interior chamber is accessible, a porous material disposed in the interior chamber, a conduit fluidly connected to the interior chamber, and a retention means for retaining positioning of the fluid collection device with respect to the wearer. The retention means of the fluid collection device may include one or more of any of the retention means disclosed herein.

The act 610 of positioning a fluid collection devices on a wearer may include positioning the opening of the fluid collection device over, near, or on the urethra of the wearer. Positioning the fluid collection device on a wearer may include positioning the opening on, around, or over the labia or vulva of the wearer. Positioning the fluid collection device on a wearer (e.g., positioning the opening adjacent to a urethra of a wearer) may include positioning the second end region of the fluid collection device against or near the perineal region of the wearer with the first end region against or near the pubic region of the wearer.

The act 620 of engaging the retention means may include engaging any of the retention means disclosed herein. The act 620 of engaging the retention means may include manipulating the retention means to engage with anatomical features of the wearer to retain the fluid collection device on the wearer. For example, engaging the retention means may include manipulating the retention means to cause at least a portion of the fluid collection device to complement the shape of the anatomy of the wearer, such as the shape in the sagittal plane from the perineal region to the pubic region of the wearer, the shape of the labia of the wearer, the space between the legs of the wearer, or the like.

In examples where the retention means includes a deformable conduit (FIGS. 2-6), engaging the retention means may include bending or shaping the deformable conduit to complement the shape of the anatomy of the wearer (such as the shape in the sagittal plane from the perineal region to the pubic region of the wearer). For example, where the deformable conduit includes gooseneck tubing having tubing disposed thereover, engaging the retention means may include manually manipulating the gooseneck tubing into a selected shape such as an arcuate shape to conform to the anatomy of the wearer along the sagittal plane from the pubic region to the perineal region of the wearer. In such examples, the opening of the fluid collection device is located over the urethra of the wearer and maintained there at least in part due to the shape of the fluid collection device that is maintained by the gooseneck tubing (which includes a fit and dimension between sections of the gooseneck tubing that allows the gooseneck tubing to maintain a shape unless a force of a selected magnitude is applied thereto). The tubing disposed over the gooseneck tubing also prevents a wearer from feeling the sections of gooseneck tubing, while also allowing urine or other fluids to be removed from the tubing, such as via vacuum.

Where the deformable conduit includes gooseneck tubing having tubing disposed thereover, engaging the retention means may include manually manipulating the gooseneck tubing into a selected shape such as an arcuate shape to conform to the shape of the wearer along the sagittal plane from the pubic region to the perineal region of the wearer. In such examples, the opening of the fluid collection device is located over the urethra of the wearer and maintained there at least in part due to the shape of the fluid collection device that is maintained by the gooseneck tubing (which includes a fit and dimension between sections of the gooseneck tubing that allows the gooseneck tubing to maintain a shape unless a force of a selected magnitude is applied thereto).

In examples, where the deformable conduit includes a plurality of fibers disposed between an inner tubing and an outer tube, engaging the retention means may include bending the deformable conduit to a selected shape. The deformable conduit with a plurality of fibers therein may be bent into a selected shape such as an arcuate shape to conform to the shape of the wearer along the sagittal plane from the pubic region to the perineal region of the wearer. In such examples, the opening of the fluid collection device is located over the urethra of the wearer and maintained there at least in part due to the shape of the fluid collection device that is maintained by the plurality of fibers. For example, as the deformable conduit is bent, the plurality of fibers may move past each other and the friction therebetween may hold them in the new position to prevent spring back.

In some examples, the retention means is at least partially defined by the porous material and the porous material includes a resilient foam that is compressible (FIG. 7). For example, the resilient foam may include a memory foam. In examples with resilient foam, engaging the retention means of the fluid collection device may include one or more of compressing, shaping, or molding the fluid collection device to a compressed state and allowing the fluid collection device to at least partially expand against the anatomy of the wearer. The fluid collection device may be biased into the anatomy of the wearer, such as with the opening over the urethra of the wearer and one or more portion of the fluid collection device may be allowed to expand to conform to the anatomy of the wearer. Accordingly, the fluid collection device may be held in place by conforming to the anatomy of the wearer, such as the labia, inner thighs, or other portions of the wearer. Such resilient foams are both porous to allow fluids to move therethrough and provide a comfortable fit between wearer and the device that does not cause sores. Engaging the retention means may include compressing the fluid collection device, disposing it in an undergarment of the wearer with the opening over the urethra, and allowing, the device to at least partially expand to the anatomy of the wearer.

In some examples, engaging the retention means includes manipulating the fluid collection device to pinch or bias against a portion of the anatomy of the wearer. In such examples, the retention means may be at least partially defined by the fluid impermeable barrier. For example, the fluid impermeable barrier defines labial flanges and lobes extending therefrom (FIGS. 9-10). In such examples, the fluid impermeable barrier converges to an apex along a longitudinal axis of a wearer facing side thereof. The labial flanges include at least semi-rigid longitudinally extending flanges having valleys sized and shaped to at least partially accommodate labia therein. The lobes extend longitudinally along at least a portion of a back side of the fluid impermeable barrier and include a valley therebetween. The lateral ends of the labial flanges rotate away from the apex when the lobes are pinched due to tension applied across the fluid impermeable barrier. Engaging the retention means of the fluid collection device may include bending or pinching the lobes of the fluid collection device and releasing the lobes when the labial flanges thereof are positioned on the labia of the wearer. As the lobes are released, the labial flanges may bias inward against the labia to compress against (e.g., pinch) the labia. Accordingly, the fluid collection device may be retained in place on the wearer by the labial flanges and apex. By locating the opening on the apex, the opening may be maintained in position over the urethra of the wearer.

In some examples, engaging the retention means may include adhering a portion of the fluid collection device to the wearer. For example, the retention means may include a mucoadhesive disposed on an outer surface of the fluid impermeable barrier in one or more regions thereon (FIGS. 11 and 12). In some examples, the one or more regions include a region bordering the opening, such as around one or more portions of the opening. Engaging the retention means includes placing the mucoadhesive of the fluid collection device in contact with the wearer, such as in contact with the inner thigh, labia, pubic region, perineal region, or the like.

In some examples, a combination of any of the retention means disclosed herein may be used together. In such examples, the engaging the retention means may include engaging multiple retention means as disclosed herein.

Receiving fluid in the fluid collection device may include receiving urine or any other fluid discharged from the wearer into the fluid collection device. The urine may be received by the porous material (such as passing from the fluid permeable membrane to the fluid permeable support). For example, receiving fluid into the fluid collection device includes receiving urine from a urethra of the wearer into the interior chamber, such as into the porous material through the opening. Receiving the fluid may include receiving the fluid into a reservoir of the fluid collection device. The fluid may be removed from the interior chamber, such as from the reservoir via the conduit therein.

The devices, systems, and methods disclosed herein provide for retention of the position of fluid collection devices with respect to the anatomy (e.g., urethra) of the wearer, thereby preventing spills of bodily fluids and soiling of beds and clothing. Such improved retention of position limits the amount of monitoring of immobile or bedbound patients to ensure the fluid collection device is in position. Such improvements limit the time that care or medical professionals need to devote for ensuring urine is not contaminating the patient, undergarments, clothing, bedding, or the like.

The method 600 may include removing the fluid from the fluid collection device via the conduit. Removing the fluid from the fluid collection device via the conduit may include applying a vacuum in the interior chamber, such as into the reservoir via the conduit. Removing the fluid from the fluid collection device via the conduit may include allowing fluid to be removed from interior chamber via gravity. Removing the fluid from the fluid collection device via the conduit may include removing the fluid into a fluid storage container, such as via vacuum or gravity feed.

While various aspects and embodiments have been disclosed herein, other aspects and embodiments are contemplated. The various aspects and embodiment disclosed herein are for purposes of illustration and are not intended to be limiting. Features from any of the disclosed embodiments may be used in combination with one another, without limitation.

What is claimed is:

1. A fluid collection device, the fluid collection device comprising:
    a fluid impermeable barrier defining an interior chamber therein, an aperture, and an opening through which the interior chamber is accessible;
    a porous material disposed in the interior chamber;
    a conduit fluidly connected to the interior chamber and extending through the aperture, wherein the porous material define a space that accommodates the conduit; and
    a retention means for retaining positioning of the fluid collection device with respect to a wearer, the retention means at least one of:
        disposed in or on the conduit, the retention means disposed in or on the conduit disposed only in the space defined by the porous material;
        including a plurality of fibers disposed between an inner tubing and an outer tube, the plurality fibers configured to move pass each other when the inner tubing and the outer tubing is bent;
        including a resilient foam that is compressible, the resilient foam forming at least a portion of the porous material; or
        including labial flanges defined by the fluid impermeable barrier, the labial flanges include at least semi-rigid longitudinally extending flanges having valleys sized and shaped to at least partially accommodate labia therein.

2. The device of claim 1 wherein the retention means includes a deformable conduit.

3. The device of claim 2 wherein the deformable conduit includes gooseneck tubing having tubing disposed thereover.

4. The device of claim 2 wherein the deformable conduit includes the plurality of fibers disposed between the inner tubing and the outer tube.

5. The device of claim 4 wherein the plurality of fibers is concentrically sandwiched between the inner tubing and the outer tube.

6. The device of claim 1 wherein;
    the retention means is at least partially defined by the porous material; and
    the porous material includes the resilient foam that is compressible.

7. The device of claim 6 wherein the resilient foam includes a memory foam.

8. The device of claim 1 wherein:
    the fluid impermeable barrier defines the labial flanges and lobes extending therefrom;
    the fluid impermeable barrier converges to an apex along a longitudinal axis of a wearer facing side thereof;
    the lobes extend longitudinally along at least a portion of a back side of the fluid impermeable barrier and include a valley therebetween; and
    lateral ends of the labial flanges rotate away from the apex when the lobes are pinched due to tension applied across the fluid impermeable barrier.

9. The device of claim 1 wherein the retention means includes a mucoadhesive disposed on an outer surface of the fluid impermeable barrier in one or more regions thereon.

10. The device of claim 9 wherein the one or more regions include a region bordering the opening.

11. A fluid collection system, comprising:
a fluid storage container configured to hold a fluid;
a fluid collection device fluidly coupled to the fluid storage container via a conduit, the fluid collection device including:
   a fluid impermeable barrier defining an interior chamber therein, an aperture, and an opening through which the interior chamber is accessible;
   a porous material disposed in the interior chamber;
   a conduit fluidly connected to the interior chamber and extending through the aperture, wherein the porous material define a space that accommodates the conduit; and
   a retention means for retaining positioning of the fluid collection device with respect to a wearer, the retention means at least one of:
      disposed in or on the conduit, the retention means disposed in or on the conduit disposed only in the space defined by the porous material;
      including a plurality of fibers disposed between an inner tubing and an outer tube, the plurality fibers configured to move pass each other when the inner tubing and the outer tubing is bent;
      including a resilient foam that is compressible, the resilient foam forming at least a portion of the porous material; or
      including labial flanges defined by the fluid impermeable barrier, the labial flanges include at least semi-rigid longitudinally extending flanges having valleys sized and shaped to at least partially accommodate labia therein; and
at least one vacuum source fluidly coupled to the fluid storage container, the at least one vacuum source configured to draw fluid into the at least one fluid storage container from the fluid collection device via the conduit.

12. The fluid collection system of claim 11 wherein the fluid storage container includes a canister.

13. The fluid collection system of claim 11 wherein the vacuum source includes one or more of a vacuum pump, a wall-mounted vacuum line, or a hand pump.

14. A method for collecting fluid, the method comprising:
positioning a fluid collection device on a wearer, the fluid collection device including:
   a fluid impermeable barrier defining an interior chamber therein and an opening through which the interior chamber is accessible;
   a porous material disposed in the interior chamber; a conduit fluidly connected to the interior chamber; and
   a retention means for retaining positioning of the fluid collection device with respect to the wearer, the retention means at least one of:
      disposed in or on the conduit, the retention means disposed in or on the conduit disposed only in the space defined by the porous material;
      including a plurality of fibers disposed between an inner tubing and an outer tube, the plurality fibers configured to move pass each other when the inner tubing and the outer tubing is bent;
      including a resilient foam that is compressible, the resilient foam forming at least a portion of the porous material; or
      including labial flanges defined by the fluid impermeable barrier, the labial flanges include at least semi-rigid longitudinally extending flanges having valleys sized and shaped to at least partially accommodate labia therein;
engaging the retention means of the fluid collection device; and
receiving fluid into the fluid collection device.

15. The method of claim 14 wherein positioning the fluid collection device on a wearer includes positioning the opening over a urethra of the wearer.

16. The method of claim 14 wherein:
the retention means includes a deformable conduit; and
engaging the retention means of the fluid collection device includes bending the deformable conduit to cause the fluid collection device to have an arcuate shape conforming to anatomy of the wearer.

17. The method of claim 16 wherein the deformable conduit includes gooseneck tubing having tubing disposed thereover.

18. The method of claim 16 wherein the deformable conduit includes the plurality of fibers disposed between the inner tubing and the outer tube.

19. The method of claim 14 wherein:
the retention means is at least partially defined by the porous material and the porous material includes the resilient foam that is compressible; and
engaging the retention means of the fluid collection device includes one or more of compressing, shaping, or molding the fluid collection device to a compressed state and allowing the fluid collection device to at least partially expand against anatomy of the wearer.

20. The method of claim 19 wherein the resilient foam includes a memory foam.

21. The method of claim 14 wherein:
the fluid impermeable barrier defines the labial flanges and lobes extending therefrom;
the fluid impermeable barrier converges to an apex along a longitudinal axis of a wearer facing side thereof;
the lobes extend longitudinally along at least a portion of a back side of the fluid impermeable barrier and include a valley therebetween; and
lateral ends of the labial flanges rotate away from the apex when the lobes are pinched due to tension applied across the fluid impermeable barrier; and
engaging the retention means of the fluid collection device includes bending or pinching the lobes of the fluid collection device and releasing the lobes when the labial flanges thereof are positioned on the labia of the wearer.

22. The method of claim 14 wherein:
the retention means includes a mucoadhesive disposed on an outer surface of the fluid impermeable barrier in one or more regions thereon; and
the retention means includes placing the mucoadhesive of the fluid collection device in contact with the wearer.

23. The method of claim 22 wherein the one or more regions include a region bordering the opening.

24. The method of claim 14 wherein receiving fluid into the fluid collection device includes receiving urine from a urethra of the wearer into the porous material.

25. The method of claim 14 further comprising removing the fluid from the fluid collection device via the conduit.

26. The method of claim 25 wherein removing the fluid from the fluid collection device via the conduit includes applying a vacuum in the interior chamber.

* * * * *